(12) United States Patent
Yoshida et al.

(10) Patent No.: US 8,241,866 B2
(45) Date of Patent: *Aug. 14, 2012

(54) METHOD FOR DETECTION OF MICROORGANISM AND KIT FOR DETECTION OF MICROORGANISM

(75) Inventors: Shinichi Yoshida, Fukuoka (JP); Takashi Soejima, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/832,740

(22) Filed: Jul. 8, 2010

(65) Prior Publication Data

US 2011/0020820 A1 Jan. 27, 2011

Related U.S. Application Data

(62) Division of application No. 11/996,422, filed as application No. PCT/JP2006/302889 on Feb. 17, 2006, now Pat. No. 8,026,079.

(30) Foreign Application Priority Data

Jul. 21, 2005 (JP) .................... 2005-211190

(51) Int. Cl.
C12Q 1/02 (2006.01)
C12Q 1/04 (2006.01)
C12Q 1/18 (2006.01)
(52) U.S. Cl. ............... 435/29; 435/32; 435/34; 435/810
(58) Field of Classification Search .................. None
See application file for complete search history.

(56) References Cited

U.S. PATENT DOCUMENTS 4,693,972 A 9/1987 Mansour et al.

FOREIGN PATENT DOCUMENTS

| JP | 6-55157 | 7/1994 |
| JP | 9-510105 | 10/1997 |
| JP | 2002-281998 | 10/2002 |
| WO | WO 95/25174 | 9/1995 |

OTHER PUBLICATIONS

Riedy, et al. "Use of a Photolabeling Technique to Identify Nonviable Cells in Fixed Homologous or Heterologous Cell Populations," *Cytometry*, vol. 12, No. 2, pp. 133-139, 1991.
Gunasekera, et al. "A Flow Cytometry Method for Rapid Detection and Enumeration of Total Bacteria in Milk," *Applied and Environmental Microbiology*, vol. 66, No. 3, pp. 1228-1232, Mar. 2000.
Marx, et al. "Covalent Attachment of Ethidium to DNA Results in Enhanced Topoisomerase II-Mediated DNA Cleavage," *Biochemistry*, vol. 36, No. 50, pp. 15884-15891, 1997.
Mukherjee, et al. "Ciprofloxacin: Mammalian DNA Topoisomerase Type II Poison In Vivo," *Mutation Research*, vol. 301, No. 2, pp. 87-92, 1993.
Rudi, et al. "Detection of Viable and Dead *Listeria monocytogenes* on Gouda-like Cheese by Real-time PCR," *Letters in Applied Microbiology*, vol. 40, pp. 301-306, 2005.
Gant, et al. "The Application of Flow Cytometry to the Study of Bacterial Responses to Antibiotics," *J. Med. Microbiol.* vol. 39, pp. 147-154, 1993.
Kobayashi, et al. "Development of a Rapid and Simple Method for Measuring Total Viable Bacterial Counts by Flow Cytometry," *Bokin Bobai*, vol. 31, No. 7, pp. 357-363, 2003, Abstract.
Bunthof, et al. "Development of a Flow Cytometric Method to Analyze Subpopulations of Bacteria in Probiotic Products and Dairy Starters," *Applied and Environmental Microbiology*, vol. 68, No. 6, pp. 2934-2942, Jun. 2002.
McClelland, et al. "Detection of *Salmonella typhimurium* in Dairy Products with Flow Cytometry and Monoclonal Antibodies," *Applied and Environmental Microbiology*, vol. 60, No. 12, pp. 4255-4262, Dec. 1994.
Froelich-Ammon, et al. "Topoisomerase Poisons: Harnessing the Dark Side of Enzyme Mechanism," *The Journal of Biological Chemistry*, vol. 270, No. 37, pp. 21429-21432, 1995.
Hooper, et al. "Fluoroquinolone Antimicrobial Agents," *The New England Journal of Medicine*, vol. 324, No. 6, pp. 384-394, 1991.
Ben Amor, et al. "Multiparametric Flow Cytometry and Cell Sorting for the Assessment of Viable, Injured, and Dead Bifidobacterium Cells during Bile Salt Stress," *Applied and Environmental Microbiology*, vol. 68, No. 11, pp. 5209-5216, Nov. 2002.
Mason, et al. "Antibacterial Action of Ciprofloxacin," *Antimicrobial Agents and Chemotherapy*, vol. 39, No. 12, pp. 2752-2758, 1995.
Santo Domingo, et al. "Evaluation of the Use of Different Antibiotics in the Direct Viable Count Method to Detect Viable Fecal Enterococci," *Abstracts of the General Meeting of the American Society for Microbiology*, vol. 100, p. 608 (session: Q-296) 2000.
Besnard, et al. "Development of a Direct Viable Count Procedure for the Investigation of VBNC State in *Listeria monocytogenes*," *Letters in Applied Microbiology*, vol. 31, pp. 77-81, 2000.
Gunasekera, et al. "Potential for Broad Applications of Flow Cytometry and Fluorescence Techniques in Microbiological and Somatic Cell Analyses of Milk," *International Journal of Food Microbiology*, vol. 85, pp. 269-279, 2003.

*Primary Examiner* — Vera Afremova
(74) *Attorney, Agent, or Firm* — Knobbe, Martens, Olson & Bear, LLP

(57) ABSTRACT

A kit is disclosed for preparing a measurement sample for detecting live cells, injured cells, VNC cells and dead microorganism cells in a test sample by the following steps:

a) the step of treating the test sample with an enzyme having an activity of decomposing cells other than those of the microorganism, colloidal particles of proteins or lipids existing in the test sample,
b) the step of treating the test sample with a topoisomerase poison and/or a DNA gyrase poison.
c) the step of treating the test sample treated in the steps a) and b) with a nuclear stain agent, and
d) the step of detecting the microorganism in the test sample treated with the nuclear stain agent by flow cytometry.

4 Claims, 23 Drawing Sheets

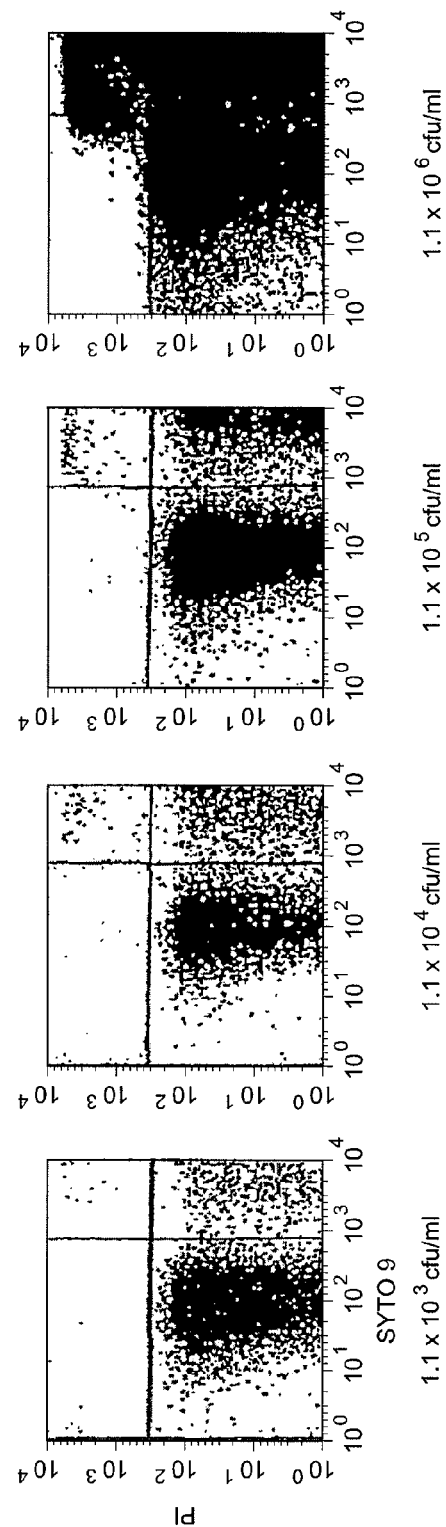
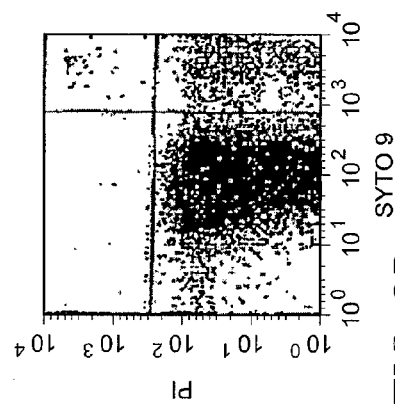
FIG. 2A
FIG. 2B

FIG. 3A
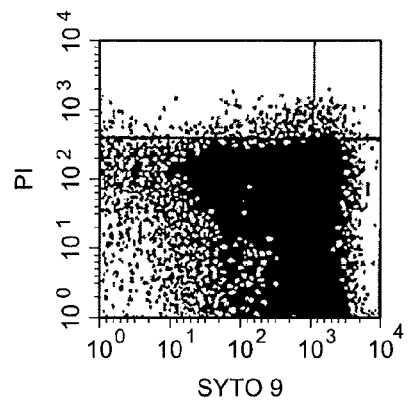
FIG. 3B
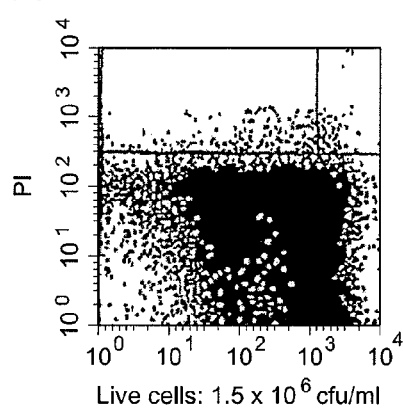 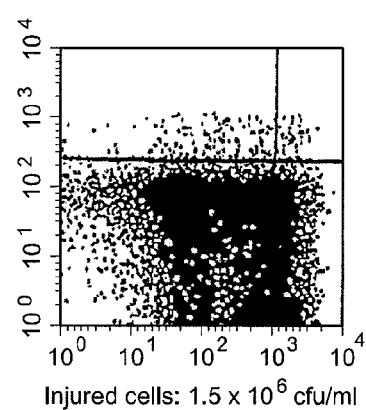
FIG. 3C
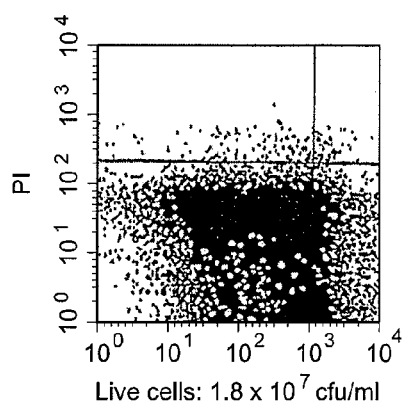 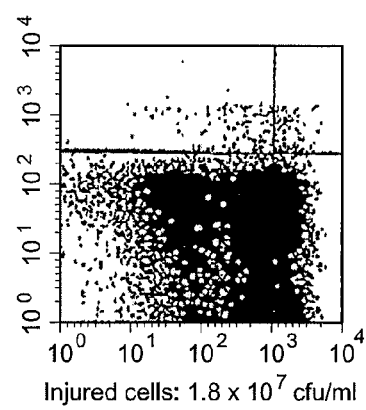

FIG. 4A
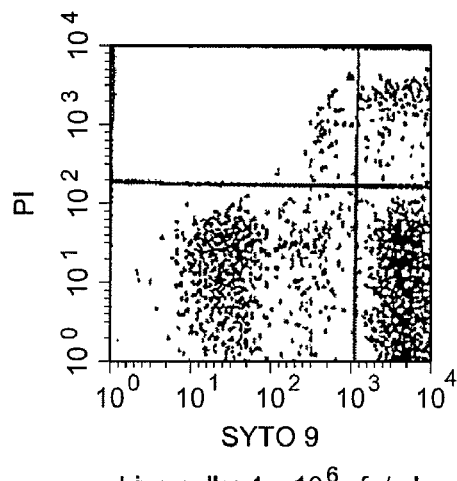
Live cells: 4 x 10⁶ cfu/ml
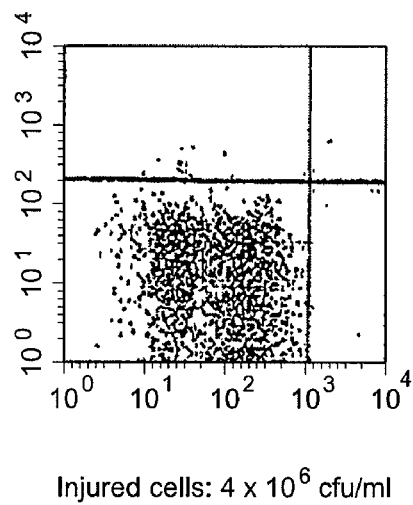
Injured cells: 4 x 10⁶ cfu/ml
FIG. 4B
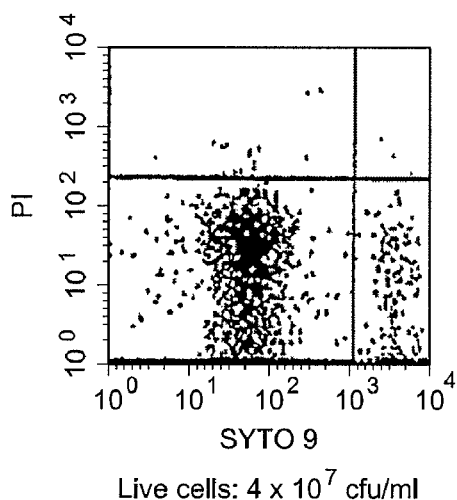
Live cells: 4 x 10⁷ cfu/ml
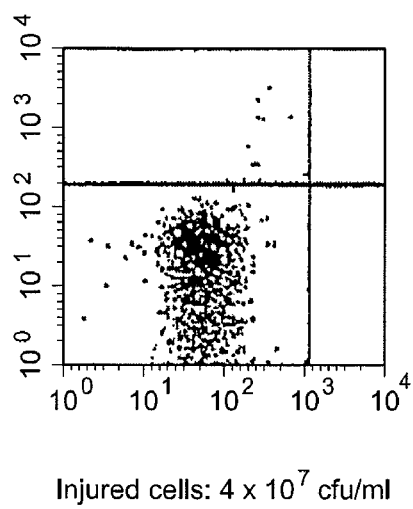
Injured cells: 4 x 10⁷ cfu/ml

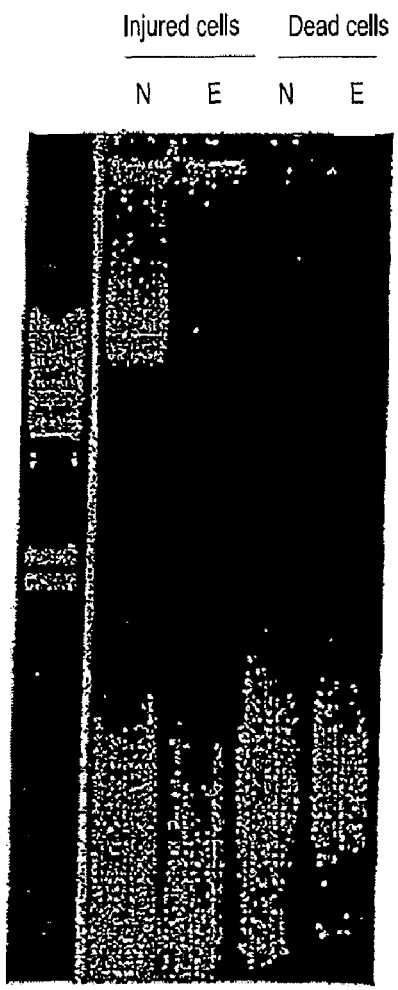 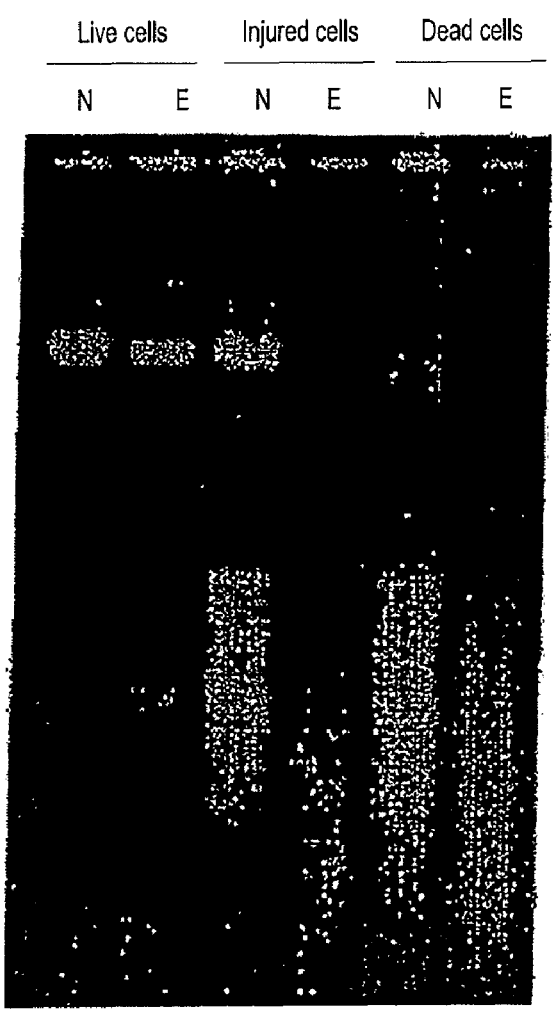
FIG. 11                    FIG. 12

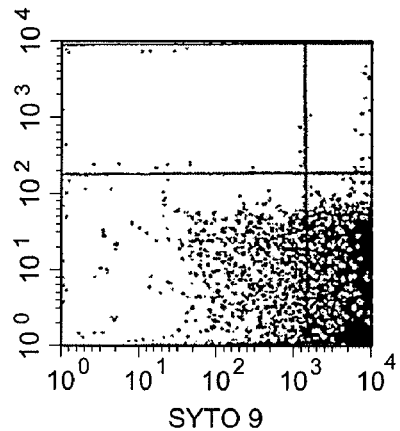
SYTO 9
Escherichia coli (live cells)
(physiological saline)
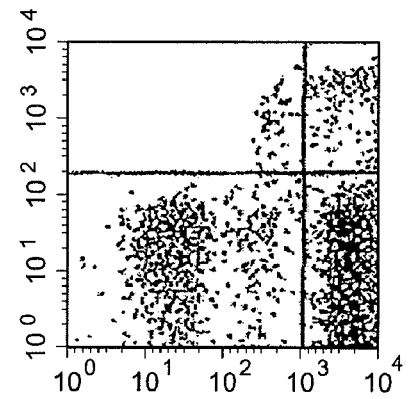
Escherichia coli (live cells) - EMA
(physiological saline)
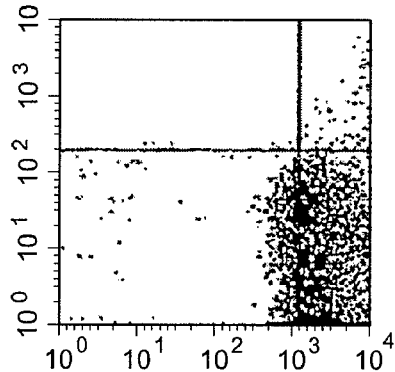
Escherichia coli (injured cells)
(physiological saline)
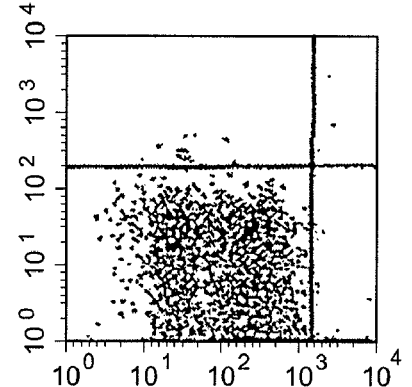
Escherichia coli (injured cells) - EMA
(physiological saline)
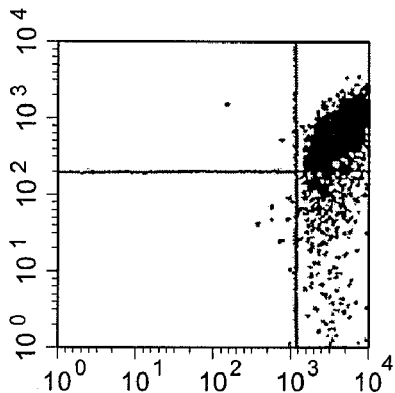
Escherichia coli (dead cells)
(physiological saline)
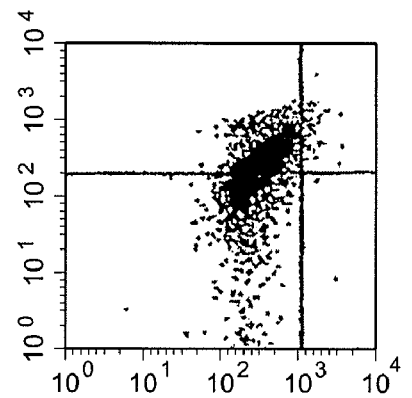
Escherichia coli (dead cells) - EMA
(physiological saline)
*FIG. 13*

Mycobacterium tuberculosis (live cells)
( 0.05% Tween80-physiological saline)

Mycobacterium tuberculosis (live cells)-EMA
( 0.05% Tween80-physiological saline)

Mycobacterium tuberculosis (injured cells)
( 0.05% Tween80-physiological saline)

Mycobacterium tuberculosis (injured cells)-EMA
( 0.05% Tween80-physiological saline)

Mycobacterium tuberculosis (dead cells)
( 0.05% Tween80-physiological saline)

Mycobacterium tuberculosis (dead cells)-EMA
( 0.05% Tween80-physiological saline)

FIG. 15

ATP method

|  | Live cells | Injured cells | Dead cells |
|---|---|---|---|
| Live cells | O | | |
| Injured cells | | | O |
| Dead cells | | | O |

Escherichia coli

|  | Live cells | Injured cells | Dead cells |
|---|---|---|---|
| Live cells | O | | |
| Injured cells | | | O |
| Dead cells | | | O |

Staphylococcus epidermidis

Method of the present invention

|  | Live cells | Injured cells | Dead cells |
|---|---|---|---|
| Live cells | O | | |
| Injured cells | | O | |
| Dead cells | | | O |

Mycobacterium tuberculosis

|  | Live cells | Injured cells | Dead cells |
|---|---|---|---|
| Live cells | O | | |
| Injured cells | | O | |
| Dead cells | | | O |

Listeria monocytogenes

*FIG. 17*

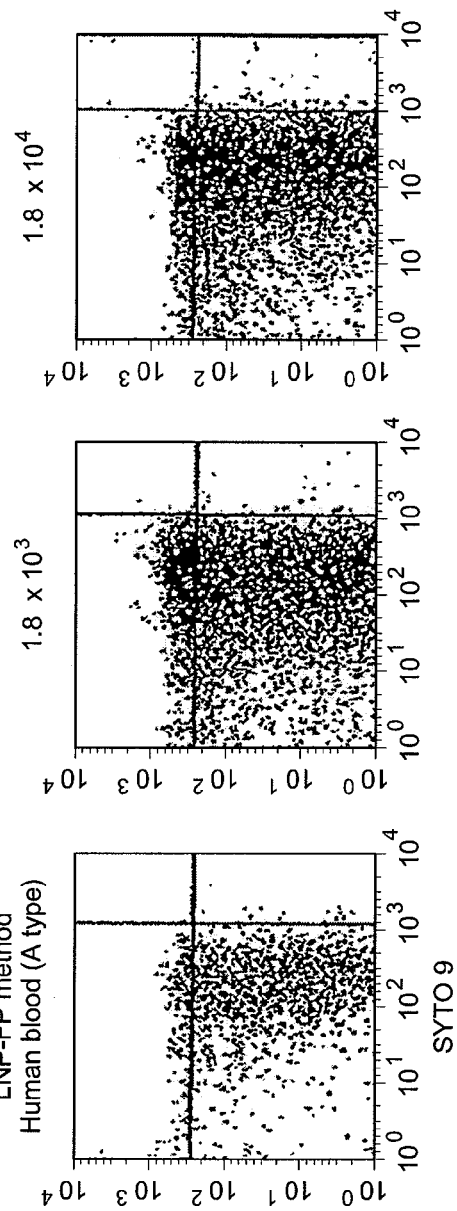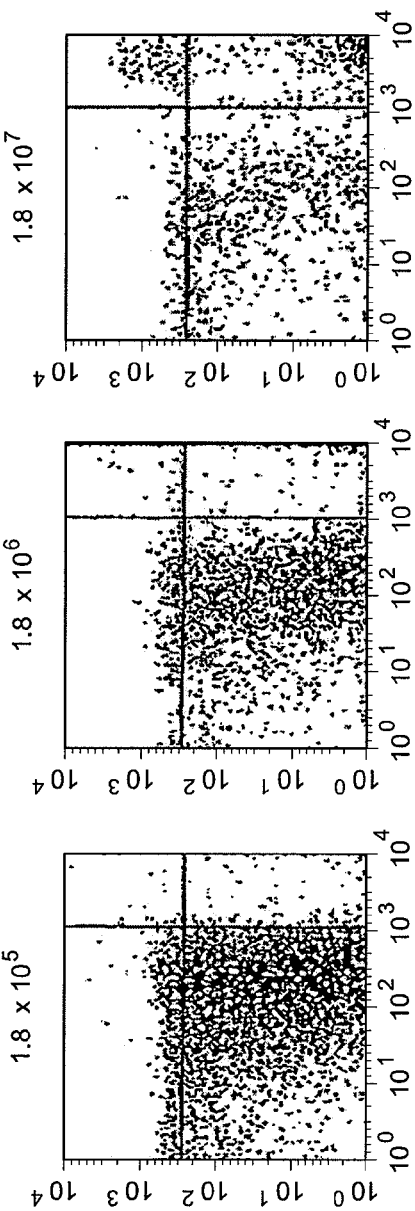
FIG. 19A

METHOD FOR DETECTION OF MICROORGANISM AND KIT FOR DETECTION OF MICROORGANISM

CROSS-REFERENCE TO RELATED APPLICATIONS

This application is a divisional of U.S. application Ser. No. 11/996,422, filed Jan. 22, 2008, now U.S. Pat. No. 8,026,079, issued Sep. 27, 2011, which is the U.S. National Phase under 35 U.S.C. §371 of International Application PCT/JP2006/302889, filed Feb. 17, 2006, which was published in a non-English language, which claims priority to JP 2005-211190, filed Jul. 21, 2005.

TECHNICAL FIELD

The present invention relates to a method for detecting a microorganism contained in foodstuffs or clinical samples, a method for preparing a sample used for the method, and a kit for detecting a microorganism. More precisely, the present invention relates to a method and a kit for detection of a microorganism that enable even distinction of live cells, injured cells and dead cells of a microorganism contained in foodstuffs or clinical samples.

BACKGROUND ART

The plate culture method has been conventionally used for measurement of general live bacterial counts in foodstuffs, clinical samples or environments. However, the plate culture method requires time of about two days to obtain a result. Furthermore, with a bacteriological test based on culture using a generally used medium, it is difficult to detect bacteria injured in environments, bacteria injured by artificial stress (the former may be referred to as Viable-but-Non Culturable (VNC) cells, and the latter may be referred to as injured cells, in particular, in narrow senses) and so forth, and it has been desired to develop a quick and reliable method for counting live bacterium.

Flow cytometry (FCM) is a technique of flowing a sample in a flow cell at a constant flow rate to pass it through a laser beam, and measuring lights scattered by cells or other microparticles or fluorescence emitted by the same. Since it enables detection of microorganisms at a single cell level, it is used in recent years for detection of microorganisms not only in the fields of molecular biology and cell biology, but also for detection of microorganisms in environment, dairy products, drink, clinical specimens and so forth (for example, Patent documents 1 and 2, Non-patent documents 1 to 5).

However, FCM apparatuses (flow cytometers) used for this method are very expensive and have a large size, and they also requires skills for operation. Moreover, they still have problems to be improved or solved concerning economy, safety, simplicity, and reliability and actuality for distinction of live cells and dead cells of microorganisms for actual applications in the fields of foodstuffs, in which a wide variety of bacteria contaminate as non-injured bacteria, injured bacteria and dead bacteria.

For example, Patent document 1 discloses a method for detecting total bacteria from a liquid sample by using an ion-chelator, a protease, a detergent and a bacteriologically specific fluorescent dye. The ion-chelator, of which typical example is EDTA, must be used at a concentration of 1 to 5 mM, and if the concentration exceeds that level, cell walls and cell membranes of live bacteria of which cell walls are not injured may also be destroyed. The preferred concentration of the ion-chelator used in the method of Patent document 1 is about 6 to 17 mM, and therefore it has a problem that both dead bacteria and live bacteria are lysed. Moreover, the detection limit of this method is around $10^4$ cfu/ml, and therefore if live bacterial count is low ($10^3$ cfu/ml or lower) in a liquid sample under a condition that only live bacteria exist in the liquid sample, the bacteria must be proliferated to a level of the aforementioned detection limit. Therefore, it cannot necessarily be considered a quick method.

Patent document 2 discloses a method of treating a body fluid sample with protease, lipase and nuclease, lysing leucocytes, thrombocytes and erythrocytes by ethidium bromide staining in a buffer comprising sodium borate, EDTA, formaldehyde and nonionic detergent (Triton X-100 etc.) to stain only bacteria with ethidium bromide, detecting and quantifying the bacteria based on fluorescence microscopy, flow cytometry, or the like. However, it is suggested that leucocytes and thrombocytes not lysed remain in the body fluid sample even after the protease, lipase and nuclease treatments, and live bacteria adsorb onto them to form complexes, and that both live bacteria and dead bacteria are stained, and thus it becomes difficult to determine whether bacteria are dead or alive. Furthermore, although Patent document 2 describes that the method is a method for detecting bacteria at a density as low as 10 cells/ml (sample) within a time of about 2 hours or shorter, often 45 minutes or shorter, it actually also discloses an example in which detection was not possible unless at least $10^4$ cfu/ml or more of bacteria exist in a body fluid sample, and thus it is not suitable for detection of a small amount of microorganisms such as those in cow's milk.

Non-patent document 1 discloses a technique of utilizing a characteristic of SYTO63 that it penetrates cell walls and cell membranes of live cells and dead cells, and a characteristic of TO-PRO3 that it penetrates only cell walls and cell membranes of dead cells to attempt distinction of live bacteria and dead bacteria based on flow cytometry. In addition, it disclose an example in which live cells and dead cells were suspended in sterilized water, and distinction of live cells and dead cells was attempted in that environment. However, the dead cells were those boiled for 15 minutes, and the cell walls and cell membranes thereof were more highly injured compared with dead bacteria in actual foodstuffs. Therefore, this technique is a technique suitable only for dead bacteria in a limited range of foodstuffs such as cooked dishes, and conditions were not examined for ultra high temperature pasteurization, which is performed for cow's milk etc. and the latest foodstuffs, and kills only bacteria without denaturing proteins in foodstuffs.

Non-patent document 2 discloses a method of allowing proteinase K to act on UHT (ultra high temperature pasteurization) cow's milk to digest micellar casein, removing lipids by refrigerated centrifugation to detect bacteria in the cow's milk, and measuring total bacterial count (including live bacteria and dead bacteria) thereof, and a method of adding 0.1% Triton X-100 as a nonionic detergent to raw milk in addition to the aforementioned proteinase K to detect bacteria in the raw milk and measuring total bacterial count (count of live bacteria and dead bacteria). However, in the methods of Non-patent document 2, even if protease K is allowed to act on UHT cow's milk, micellar casein is not completely digested, and there are a lot of incomplete digestion products having a size comparable to those of bacteria. If a fluorescent nuclear stain agent such as SYTO BC or SYTO9 is made to act on such products, strong nonspecific adsorption occurs to make the distinction of them from live bacteria difficult. Moreover, it has also a problem that cell membranes of somatic cells such as bovine leucocytes and mammary epitheliocyte, considered as one of the contaminant milk components, are only slightly injured, and if they are subjected to staining with SYTO BC, SYTO9 or propidium iodide as they are, propidium iodide does not penetrate into them, and as a result, green fluorescence is emitted by chromosomal DNA to make distinction of the somatic cells from live bacteria difficult.

Non-patent document 3 discloses a method similar to the method of Patent document 1 except that the protease treatment is excluded as a method for measuring live bacterial count of lactic acid bacteria in yogurt or yogurt starter, and the method is described as a method of using a nonionic detergent and a chelating agent in combination. As the characteristic of the invention, it is described that the method enables destruction of somatic cells as contaminants and effective separation of fat globules. However, samples subjected to the aforementioned treatment contain a lot of contaminants originating in milk, and the detection limit for live lactic acid bacteria is degraded to a level as low as about $10^5$ cfu/ml for yogurt or yogurt starter due to the contaminants. Therefore, the method requires extremely delicate determination of conditions for destroying only somatic cells and not injuring cell walls and cell membranes of live bacteria by adjusting the concentrations of the nonionic detergent and the chelating agent. Thus, the method is not suitable as a convenient and highly sensitive detection method for distinguishing live bacteria and dead bacteria.

Although ethidium monoazide (EMA, 8-azido-3-amino-6-phenyl-5-ethylphenanthradinium chloride) is generally known for the effect as an anticancer agent, it is a poison against topoisomerase II (type II topoisomerase) existing in mammalian cells (for example, Non-patent document 5). EMA disorderly intercalates into chromosomal DNAs, and then only intercalating EMA is converted into nitrene by irradiation of visible light, and binds to the chromosomal DNAs by covalent attachment. For example, by the action of topoisomerase, cancer cells adjust the helical degree of the DNA strands, or rewind DNA strands in order to perform replication of the DNA strands and gene expression (transcription of DNA), and the rewinding is achieved by cleavage of corresponding sites of the chromosomal DNAs and religation of the cleavage products. In this occasion, as for the function of EMA, the religation of DNAs by topoisomerase II is inhibited by the action of covalent attachment of nitrene derived from EMA at the time of the religation, and the fragmentation of the chromosomal DNAs is enhanced as a result. EMA not intercalating into DNA strands and existing in a free form is converted into hydroxylamine by visible light, but the hydroxylamine does not inhibit the activity of topoisomerase II.

As substances inhibiting such an activity of topoisomerase II, there are known, besides ethidium monoazide mentioned above, amsacrine, doxorubicin, ellipticine, etoposide, mitoxantrone, saintopin, and so forth. As substances inhibiting the activity of topoisomerase I, which has an activity similar to that of topoisomerase II, there are known camptothecin, topotecan, and so forth (for example, Non-patent document 6). Further, in the field of bacteria, as substances inhibiting the activity of bacterial DNA gyrase having an activity similar to those of the aforementioned enzymes, there are known ciprofloxacin, ofloxacin, enoxacin, pefloxacin, fleroxacin, norfloxacin, nalidixic acid, oxolinic acid, piromidic acid, and so forth (for example, Non-patent document 7).

However, there has not so far been reported at all use of these topoisomerase I poisons, topoisomerase II poisons, and bacterial DNA gyrase poisons for pretreatments of samples such as foodstuffs and clinical samples containing microorganisms in a test method for distinguishing live cells and dead cells of a microorganism for the purpose of realizing quick and highly sensitive detection.

As another method for detecting live bacteria, there has been proposed an automated system for conveniently and quickly detecting respiratory activity and esterase activity (Patent document 3). However, detection by this method is limited to a case where respiratory activity and esterase activity of the objective bacterium can be accurately measured.

As the state of microorganisms other than live bacteria, there are injured cells, VNC (Viable-but-Non Culturable) cells and dead cells. There is disclosed a method for detecting them by flow cytometry using cFDA (carboxyfluorescein diacetate), which emits green fluorescence in the presence of esterase, and propidium iodide (PI) (Non-patent document 8). However, this method is also a method that can clearly distinguish live cells, injured cells and dead cells only when the injury to cell walls of the injured cells comparatively advances. Therefore, when the injured cells are those showing a low degree of injury caused by low temperature long time pasteurization (LTLT) or high temperature short time pasteurization (HTST), or those showing a low degree of injury due to stress in environment, live cells and injured cells cannot be distinguished by this method.

Patent document 1: International Patent Application Unexamined Publication in Japan No. 9-510105
Patent document 2: Japanese Patent Publication (Kokoku) No. 6-55157
Patent document 3: Japanese Patent Laid-open No. 2002-281998
Non-patent document 1: Bokin Bobai, Vol. 31, No. 7, 2003, pp. 357-363
Non-patent document 2: Applied and Environmental Microbiology, Vol. 66, No. 3, 2000, pp. 1228-1232
Non-patent document 3: Applied and Environmental Microbiology, Vol. 68, No. 6, 2002, pp. 2934-2942
Non-patent document 4: Applied and Environmental Microbiology, Vol. 60, No. 12, 1994, pp. 4255-4262
Non-patent document 5: Biochemistry, Vol. 36, No. 50, 1997, pp. 15884-15891
Non-patent document 6: The Journal of Biological Chemistry, Vol. 270, No. 37, 1995, pp. 21429-21432
Non-patent document 7: The New England Journal of Medicine, Vol. 324, No. 6, 1991, pp. 384-394
Non-patent document 8: Applied and Environmental Microbiology, Vol. 68, 2002, pp. 5209-5216

DISCLOSURE OF THE INVENTION

Problems to be solved by the Invention

An object of the present invention is to provide a method for detecting a microorganism, which enables convenient and quick detection of live microorganisms in foodstuffs and clinical samples by using economically advantageous flow cytometry, and is applicable to spontaneous inspections in food factories or clinical field, and a method for preparing a sample used for the foregoing method. Moreover, another object of the present invention is to provide a kit enabling distinction of live cells, injured cells and dead cells.

Means for Solving the Problem

In view of the aforementioned background, the inventors of the present invention assiduously researched on a convenient test method with certainty and actuality for detection of live cells of a microorganism contained in foodstuffs and clinical samples, in particular, for distinction of live cells, injured cells and dead cells. As a result, they found that even if the amount of the microorganism contained in a sample is extremely small, it is possible to distinct live cells and dead cells high-sensitively by identifying various contaminants including dead cells contained in foodstuffs and clinical samples, pretreating the foodstuff or clinical sample with lipase, protease, ethidium monoazide as a DNA intercalating agent and so forth in order to efficiently remove the contaminants in the step for a pretreatment of the sample, staining with fluorescence the sample, and subjecting to measurement using a flow cytometer. Thus, they accomplished the present invention.

That is, the present invention provides a method for preparing a measurement sample for detecting live cells of a microorganism in a test sample by flow cytometry, which comprises the following steps:
a) the step of treating the test sample with an enzyme having an activity of decomposing cells other than those of the microorganism, colloidal particles of proteins or lipids existing in the test sample, and
b) the step of treating the test sample with a topoisomerase poison and/or a DNA gyrase poison.

The present invention also provides a method for detecting live cells of a microorganism in a test sample by flow cytometry, which comprises the following steps:
a) the step of treating the test sample with an enzyme having an activity of decomposing cells other than those of the microorganism, colloidal particles of proteins or lipids existing in the test sample,
b) the step of treating the test sample with a topoisomerase poison and/or a DNA gyrase poison.
c) the step of treating the test sample treated in the steps a) and b) with a nuclear stain agent, and
d) the step of detecting the microorganism in the test sample treated with the nuclear stain agent by flow cytometry.

In preferred embodiments of the method for preparing a measurement sample for detecting live cells of a microorganism in a test sample by flow cytometry and the method for detecting live cells of a microorganism in a test sample by flow cytometry, the step b) is performed after the step a).

In preferred embodiments of the aforementioned methods, the test sample is one of milk, a dairy product, a foodstuff produced from milk or a dairy product as a raw material, a blood sample, a urine sample, a spinal fluid sample, a synovial fluid sample and a pleural fluid sample.

In preferred embodiments of the aforementioned methods, the microorganism is a bacterium.

In preferred embodiments of the aforementioned methods, the enzyme is selected from lipolytic enzymes and proteases.

In preferred embodiments of the aforementioned methods, the topoisomerase poison is selected from amsacrine, camptothecin, doxorubicin, ellipticine, etoposide, mitoxantrone, saintopin, topotecan and CP-115,953.

In preferred embodiments of the aforementioned methods, the DNA gyrase poison is selected from ciprofloxacin, ofloxacin, enoxacin, pefloxacin, fleroxacin, norfloxacin, nalidixic acid, oxolinic acid and piromidic acid.

In preferred embodiments of the aforementioned methods, the topoisomerase poison is ethidium monoazide, and the method comprises the step of subjecting the test sample to which ethidium monoazide is added to irradiation of visible light.

In preferred embodiments of the aforementioned methods, the methods further comprises the step c) of treating the test sample treated in the steps a) and b) with a nuclear stain agent.

In preferred embodiments of the aforementioned methods, the nuclear stain agent comprises a first stain agent that can penetrate cell walls of live cells and dead cells, and a second stain agent that more easily penetrate cell walls of dead cells than those of live cells compared with the first stain agent.

In preferred embodiments of the aforementioned methods, the nuclear stain agent is propidium iodide and SYTO9.

The present invention also provides a kit for preparing a measurement sample for detecting live cells of a microorganism in a test sample by flow cytometry, which comprises the following elements:
an enzyme selected from lipolytic enzymes and proteases,
a topoisomerase poison and/or a DNA gyrase poison, and
a nuclear stain agent.

In a preferred embodiment of the aforementioned kit, the topoisomerase poison is selected from amsacrine, camptothecin, doxorubicin, ellipticine, etoposide, mitoxantrone, saintopin, topotecan and CP-115,953.

In a preferred embodiment of the aforementioned kit, the DNA gyrase poison is selected from ciprofloxacin, ofloxacin, enoxacin, pefloxacin, fleroxacin, norfloxacin, nalidixic acid, oxolinic acid and piromidic acid.

In a preferred embodiment of the aforementioned kit, the topoisomerase poison is ethidium monoazide.

ADVANTAGEOUS EFFECT OF THE INVENTION

The present invention enables convenient and quick distinction of live cells, injured cells and dead cells in foodstuffs and clinical samples by flow cytometry. The methods and kit of the present invention can be applied to spontaneous inspections, and are also economically advantageous.

BRIEF DESCRIPTION OF THE DRAWINGS

[FIG. 2] Graphs showing the results of FCM measurement after SYTO9/PI staining. FIG. 2A shows LP-treated UHT homogenized milk not inoculated with the bacteria. FIG. 2B shows LP-treated UHT homogenized milk inoculated with *Escherichia coli* (live bacteria).

[FIG. 3] Graphs showing the results of FCM measurement after SYTO9/PI staining. FIG. 3A shows LP-treated LTLT non-homogenized milk not inoculated with bacteria. FIG. 3B shows LP-treated LTLT non-homogenized milk inoculated with *Escherichia coli* (live bacteria and injured bacteria), and FIG. 3C shows LP-treated LTLT non-homogenized milk inoculated with *Staphylococcus epidermidis* (live bacteria and injured bacteria).

[FIG. 4] Graphs showing the results of FCM measurement after SYTO9/PI staining. FIG. 4A shows LP-treated and EMA-treated *Escherichia coli* suspensions (live bacteria and injured bacteria) and FIG. 4B shows *Staphylococcus epidermidis* suspensions (live bacteria and injured bacteria).

[FIG. 5] Graphs showing the results of FCM measurement after SYTO9/PI staining.

[FIG. 6] Graphs showing the results of FCM measurement after SYTO9/PI staining for LP-treated and EMA-treated non-homogenized milk inoculated with *Escherichia coli* (live bacteria and injured bacteria).

[FIG. 7] Graphs showing the results of FCM measurement after SYTO9/PI staining.

[FIG. 8] Graphs showing the results of FCM measurement after SYTO9/PI staining for UHT homogenized milk inoculated with *Escherichia coli* (live bacteria) and *Staphylococcus epidermidis* (live bacteria) after LP-treatment and a) amsacrine, b) ellipticine, c) camptothecin or d) ciprofloxacin treatment.

[FIG. 11] Electrophoresis photographs of chromosomal DNAs of *Escherichia coli* (injured bacteria and dead bacteria) extracted and purified before (N) or after (E) the EMA treatment.

[FIG. 12] Electrophoresis photographs of chromosomal DNAs of *Staphylococcus epidermidis* (live bacteria, injured bacteria and dead bacteria) extracted and purified before (N) or after (E) the EMA treatment.

[FIG. 13] Graphs showing the results of FCM measurement for live bacteria, injured bacteria and dead bacteria of *Escherichia coli* before and after the EMA treatment.

[FIG. 15] Graphs showing the results of FCM measurement for live bacteria of *Mycobacterium tuberculosis* and injured bacteria and dead bacteria of the same treated with isonicotinic acid hydrazide and rifampicin before and after the EMA treatment.

[FIG. 17] Graphs showing correspondence of classifications of live bacteria, injured bacteria and dead bacteria of *Escherichia coli, Staphylococcus epidermidis, Mycobacterium tuberculosis* and *Listeria* according to the ATP method, and distinction of the same according to the method of the present invention.

[FIG. 19] Graphs showing the results of FCM measurement for *Listeria* in human blood before or after the EMA treatment. FIG. 19A shows LNP-FP method.

BEST MODE FOR CARRYING OUT THE INVENTION

Figure 1:
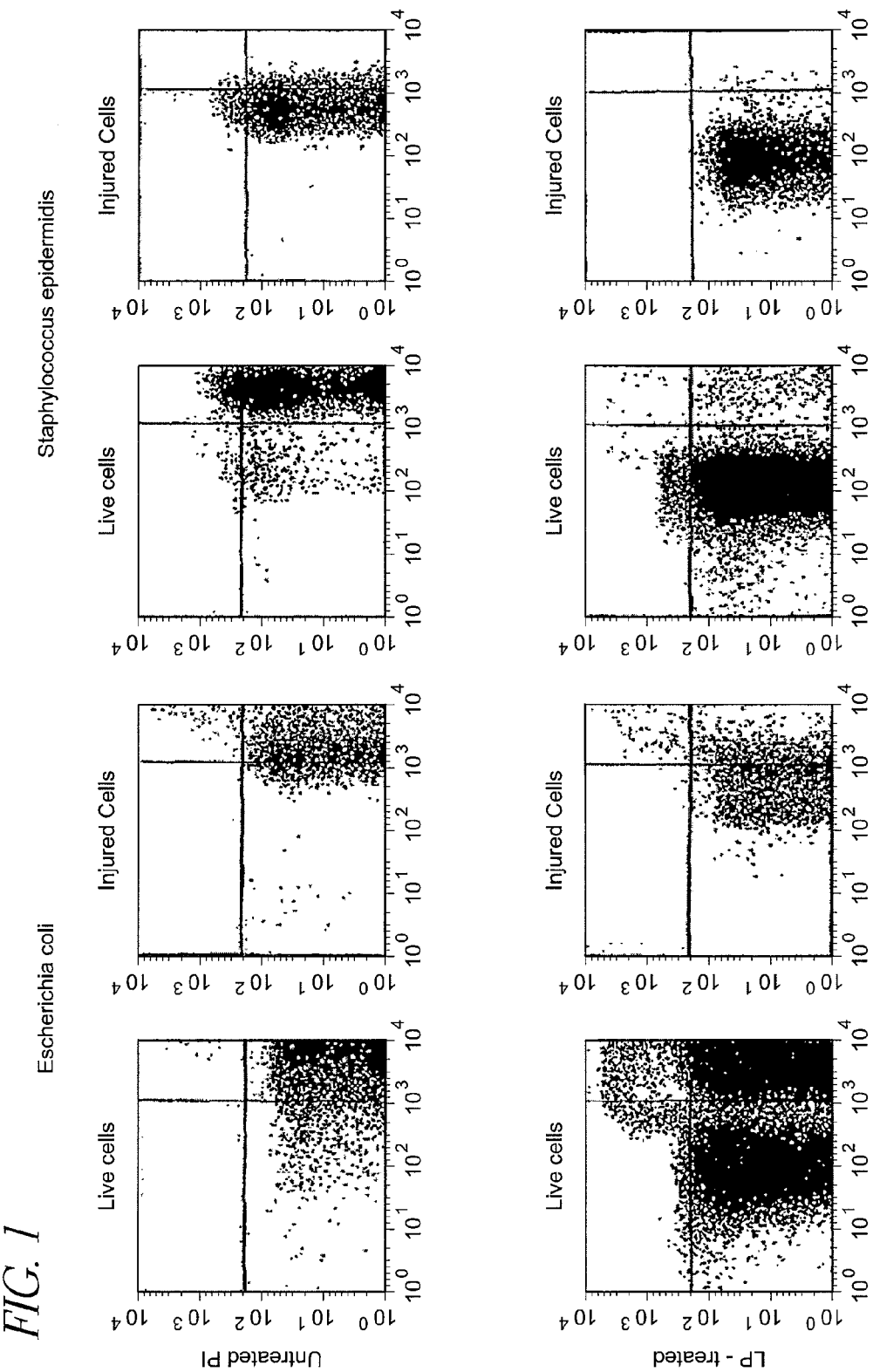
[FIG. 1] Graphs showing the results of FCM measurement after SYTO9/PI staining for LP-treated group *Escherichia coli* suspensions (live bacteria and injured bacteria) and LP-treated group *Staphylococcus epidermidis* suspensions (live bacteria and injured bacteria) as well as untreated group *Escherichia coli* suspensions (live bacteria and injured bacteria) and untreated group *Staphylococcus epidermidis* suspensions (live bacteria and injured bacteria).

Hereafter, preferred embodiments of the present invention will be explained in detail. However, the present invention is not limited to the following preferred embodiments, and can be freely modified within the scope of the present invention.

The method for preparing a measurement sample for flow cytometry (henceforth also abbreviated as "FCM") according to the present invention is a method for preparing a measurement sample for detecting live cells of a microorganism in a test sample by flow cytometry, and is a method comprising the following steps:
a) the step of treating the test sample with an enzyme having an activity of decomposing cells other than those of the microorganism, colloidal particles of proteins or lipids existing in the test sample, and
b) the step of treating the test sample with a topoisomerase poison and/or a DNA gyrase poison.

The method for detecting live cells of a microorganism in a test sample is a method for detecting the live cells using a sample obtained by the aforementioned method for preparing a measurement sample for FCM, and further comprises the following step in addition to the aforementioned steps a) and b):
c) the step of treating the test sample treated in the steps a) and b) with a nuclear stain agent, and
d) the step of detecting the microorganism in the test sample treated with the nuclear stain agent by flow cytometry.

In this specification, the "test sample" means an object for which live cells of a microorganism existing therein are detected, and it is not particularly limited so long as the microorganism can be detected by FCM. Examples include milk, dairy products, and foodstuffs using milk or a dairy product as a raw material, blood samples, urine samples, spinal fluid samples, synovial fluid samples, pleural fluid samples, and so forth. Milk, dairy products, foodstuffs using milk or a dairy product as a raw material are especially preferred. In the present invention, the test sample may be any one of the aforementioned products and biosamples itself, and may be one obtained by diluting or concentrating any one of the aforementioned products and biosamples or subjecting any one of the aforementioned products and biosamples to a pretreatment other than the treatment according to the method of the present invention. Examples of the pretreatment include heat treatment, filtration, treatment with an antibiotic, and so forth.

The "microorganism" is an object to be detected by the method of the present invention, and is not particularly limited so long as it can be detected by FCM, and the topoisomerase poison, DNA gyrase poison, or ethidium monoazide differently act on live cells, injured cells and dead cells of the microorganism. Preferred examples include bacteria, filamentous fungi, yeasts, and so forth. The bacteria include both gram-positive bacteria and gram-negative bacteria. Examples of the gram-positive bacteria include *Staphylococcus* bacteria such as *Staphylococcus epidermidis, Streptococcus* bacteria, *Listeria* bacteria, *Bacillus* bacteria, *Mycobacterium* bacteria, and so forth. Examples of the gram-negative bacteria include *Escherichia* bacteria such as

*Escherichia coli*, enteric bacteria as typified by *Enterobacter* bacteria, *Salmonella* bacteria, *Vibrio* bacteria, *Pseudomonas* bacteria, and so forth.

In the present invention, the "live bacteria (live cell)" refers to a cell that can proliferate when it is cultured under a generally preferred culture condition, and can proliferate in a state that the cell exhibits metabolic activities of the cell (Viable-and-Culturable state) under the preferred condition, and is a cell substantially free from injury of cell wall. As the metabolic activities mentioned above, ATP activity, esterase activity etc. can be exemplified.

The "injured bacteria" (injured cell or Viable-but-Non Culturable cell) is a cell in a state that it hardly proliferates even when it is cultured under an optimum culture condition, because it is injured due to artificial stress or environmental stress, and it shows metabolic activities at a lower level compared with a live cell, but a significant level compared with a dead cell (injured or Viable-but-Non Culturable [VNC] state). Although VNC cells and injured cells may be distinguished in a narrow sense on the basis of the type of stress as the cause of the injury, VNC cells and injured cells in narrow senses may be collectively called injured cells in the present invention in contrast with live cells or dead cells.

Detection of bacteria exhibiting the state of injured cell by using mild heat treatment or administration of antibiotics is attracting attention particularly in the field of food sanitation inspection and clinical test, and the present invention provides a method for detecting a microorganism, which enables distinction of all states of cells including not only detection of live cells, but also distinction of live cells and dead cells, and distinction of live cells and injured cells.

The "dead cell" is a cell in a state that it cannot proliferate, does not exhibit metabolic activities (dead state), even if it is cultured under an optimum culture condition. Moreover, it is in a state that although structure of cell wall is maintained, the cell wall itself is highly injured, and a nuclear stain agent exhibiting weak permeability such as propidium iodide can penetrate the cell wall.

The unit of cell number of live cells, injured cells and dead cells is usually represented by cell number (cells)/ml. The number of live cells can be approximated with a number of colonies (cfu/ml (colony forming units/ml)) formed by culturing the cells under an optimum condition on a suitable plate medium. A standard sample of dead cells can be prepared by subjecting a live cell suspension to a heat treatment, for example, a heat treatment in boiling water. In this case, the number of dead cells in such a sample can be approximated with cfu/ml of the live cell suspension before the heat treatment. Although time of the heat treatment in boiling water for preparing dead cells varies depending on type of microorganism, dead cells of the bacteria described in the examples, for example, can be prepared by a heat treatment of about 12 minutes. Injured cells can be prepared by a heat treatment in boiling water for a shorter time compared with that used for the preparation of dead cells. For example, injured cells of the bacteria described in the examples can be prepared by a heat treatment of about 50 seconds. In this case, the number of injured cells can be approximated with cfu/ml of the live cell suspension before the heat treatment. Further, a standard sample of injured cells can also be prepared by a treatment with an antibiotic. In such a case, the cell number of injured cells can be approximated with the number of colonies (cfu/ml) formed when the cells are cultured under an optimum condition on a suitable plate medium, by removing the antibiotic after treating live cell suspension with the antibiotic, measuring transmittance of visible light (wavelength: 600 nm), that is turbidity, and comparing the turbidity with that of a live cell suspension which density of live cell is known.

The "colloidal particles of proteins" are colloidal particles contained in a test sample, comprising proteins as constituents, and dyed nonspecifically with a nuclear stain agent, and examples of which include micellar casein.

Hereafter, the method of the present invention will be explained for every step.

(1) Step a)

In this step, a test sample is treated with an enzyme having an activity for decomposing cells other than the microorganism, colloidal particle of proteins or lipids existing in the test sample.

It is generally said that in order to detect bacteria by FCM, the bacteria should be subjected to pass through a detector in an amount of at least about 100 cfu. However, when live cells in a test sample such as milk are detected by FCM, a large amount of contaminant components such as somatic cells, fat globules and micellar casein, not only the bacteria, invade into a gate (bacterial gate) on FSC (Forward Scattered Light)-SSC (Side Scattered Light), and therefore bacteria may not be detected even if about 100 cfu of them pass through the detector. Therefore, it is preferable to remove or reduce cells other than the microorganism, colloidal particles of proteins, lipids and so forth existing in the test sample by a treatment with an enzyme.

In the case that the test sample is milk, a dairy product or a foodstuff produced from milk or a dairy product as a raw material, examples of the cells other than the microorganism existing in the test sample include bovine leucocytes, mammary epitheliocytes and so forth. Furthermore, in the case that the test sample is a biosample such as blood sample, urine sample, spinal fluid sample, synovial fluid sample or pleural fluid sample, examples of the cells include erythrocytes, leucocytes (granulocytes, neutrophils, basophils, monocytes, lymphocytes etc.), thrombocytes, and so forth.

The enzyme aforementioned above is not particularly limited, so long as an enzyme that can decompose the aforementioned contaminants and does not injure live cells of the microorganism as a detection object is chosen, and examples of which include lipolytic enzymes and proteases. Although one kind of enzyme may be independently used, or two or more kinds of enzymes may be used in combination as the enzyme, it is preferable to use both a lipolytic enzyme and a protease.

Examples of lipolytic enzyme include lipases, phosphatases and so forth, and examples of the protease include proteinase K, pronase and so forth.

Although conditions for the treatment with these enzymes are not particularly limited, and can be suitably determined, for example, conditions of a final concentration of 10 to 50 U/ml, a temperature of 25 to 37° C., and a treatment time of 30 minutes or more can be mentioned for lipases, and conditions of a final concentration of 10 to 50 U/ml, a temperature of 25 to 37° C., and a treatment time of 30 minutes or more can be mentioned for proteinase K.

The treatments with a lipolytic enzyme and a protease are preferably performed in the order of (i) the treatment with a lipolytic enzyme and (ii) the treatment with a protease, or the treatment may be performed by simultaneously adding them. Although these enzymes may be allowed to exist in the test sample after the treatment, it is preferable to separate the enzymes from the cells by centrifugation or the like.

(2) Step b)

In this step, the test sample is treated with a topoisomerase poison and/or a DNA gyrase poison. The step b) is preferably performed after the step a).

The topoisomerase poison and the DNA gyrase poison used for the present invention refer to those not inhibiting the activities of topoisomerase and DNA gyrase for cleaving DNAs, respectively, but inhibiting religation of DNAs, or enhancing forward rate of DNA cleavage. The topoisomerase poison and the DNA gyrase poison are preferably those that bind to chromosomal DNAs of a microorganism by covalent attachment, those that intercalate into the chromosomal DNAs and bind to chromosomal DNAs by covalent attachment upon irradiation of visible light, those that simply intercalate into the chromosomal DNAs, or those that form a complex with topoisomerase or DNA gyrase.

Although it is preferable to use both the topoisomerase poison and DNA gyrase poison, either one may also be used.

The topoisomerase poison and the DNA gyrase poison are preferably those exhibiting different actions on live cells, and injured cells, dead cells, somatic cells such as bovine leucocytes, leucocytes and thrombocytes etc., more specifically, those exhibiting higher permeability for cell walls of injured cells and dead cells and cell membranes of somatic cells such as bovine leucocytes, leucocytes and thrombocytes etc., compared with that for cell walls of live cells.

Examples of the topoisomerase poison include amsacrine, camptothecin, doxorubicin, ellipticine, etoposide, mitoxantrone, saintopin, topotecan, CP-115,953, and so forth. One kind of topoisomerase poison may be independently used, or two or more kinds of them may used in combination.

Examples of the DNA gyrase poison include ciprofloxacin, ofloxacin, enoxacin, pefloxacin, fleroxacin, norfloxacin, nalidixic acid, oxolinic acid, piromidic acid, and so forth. One kind of DNA gyrase poison may be independently used, or two or more kinds of them may used in combination.

The conditions for the treatment with the topoisomerase poison or DNA gyrase poison may be suitably determined. For example, conditions that enables easy distinction of live cells from injured cells and dead cells can be determined by adding a topoisomerase poison or DNA gyrase poison at various concentrations to suspensions of live cells, injured cells and dead cells of the microorganism as an object of detection, leaving them for various periods of time, then harvesting the cells by centrifugation or the like, staining the cells with a nuclear stain agent, and analyzing the cells by FCM. Furthermore, conditions that enables easy distinction of live cells of the microorganism as an object of detection from somatic cells such as bovine leucocytes, thrombocytes and the like can be determined by adding a topoisomerase poison at various concentrations to suspensions of the live cells and the aforementioned various cells (live cells containing injured cells), leaving them for a predetermined time, then harvesting the live cells and the aforementioned various cells by centrifugation or the like, staining the cells with a nuclear stain agent, and analyzing the cells by FCM. Examples of such conditions include, specifically, a final concentration of 1 to 100 µg/ml, temperature of 25 to 37° C., and treatment time of 5 minutes to 48 hours for amsacrine, a final concentration of 0.05 to 5 µg/ml, temperature of 25 to 37° C., and treatment time of 10 minutes to 48 hours for ellipticine, a final concentration of 1 to 100 µg/ml, temperature of 25 to 37° C., and treatment time of 10 minutes to 48 hours for camptothecin, a final concentration of 0.4 to 40 µg/ml, temperature of 25 to 37° C., and treatment time of 10 minutes to 48 hours for ciprofloxacin, a final concentration of 1 to 100 µg/ml, temperature of 25 to 37° C., and treatment time of 5 minutes to 48 hours for etoposide, and a final concentration of 0.1 to 10 µg/ml, temperature of 25 to 37° C., and treatment time of 10 minutes to 48 hours for mitoxantrone. After the test sample is treated under the predetermined conditions, the treatment is preferably terminated by elimination by dilution, and/or centrifugal separation or the like.

The aforementioned topoisomerase poison and DNA gyrase poison are more likely to penetrate cell walls of injured cells and dead cells compared with cell walls of live cells. Therefore, it is considered that if the treatment time is within the ranges mentioned above, the poisons do not substantially penetrated cell walls of live cells, but they penetrate into injured cells, dead cells and live somatic cells including injured cells, since they have only cell membranes not including cell walls. It is estimated that the topoisomerase poison or DNA gyrase poison penetrates into somatic cells, injured cells and dead cells, then disorderly bind to chromosomal DNAs by covalent attachment, intercalates into the DNAs, or forms a complex with the topoisomerase, and further inhibits religation of the DNAs by topoisomerase II or topoisomerase I in somatic cells, or topoisomerase IV, or topoisomerases I, III or DNA gyrase in injured cells, or enhances the forward rate of DNA cleavage to cause fragmentation of the chromosomal DNAs.

It is considered that if the chromosomal DNAs of injured cells are preferentially fragmented compared with those of live cells, in staining with a nuclear stain agent that penetrates cell walls of live cells, injured cells and dead cells, such as SYTO9, staining intensity of injured cells is suppressed compared with that of live cells, and as a result, it becomes possible to distinguish the live cells and injured cells in the detection by FCM.

In another preferred embodiment of the present invention, the topoisomerase poison is ethidium monoazide, and the method comprises the step of subjecting the test sample, to which ethidium monoazide is added, to irradiation of visible light. Ethidium monoazide (EMA) is more likely to penetrate cell walls of injured cells compared with cell walls of live cells of microorganisms. Therefore, it is considered that EMA does not substantially penetrate cell walls of live cells, but it penetrates cell walls of injured cells and cell membranes of live somatic cells including injured cells, since the cell membranes thereof are not cell walls. When leucocytes and thrombocytes in blood are live cells, EMA becomes more likely to penetrate cell membranes of the cells in sterilized water or a hypotonic salt solution. EMA penetrates into somatic cells and injured cells, and disorderly intercalates into chromosomal DNAs, and then only intercalating EMA is converted into nitrene by irradiation of visible light, and binds to the chromosomal DNAs by covalent attachment. It is estimated that then it inhibits religation of the DNAs by topoisomerase II in somatic cells, topoisomerase IV in injured cells, or DNA gyrase to cause fragmentation of the chromosomal DNAs.

Conditions for the treatment with EMA can be appropriately determined. For example, conditions that enables easy distinction of live cells from injured cells can be determined by adding EMA at various concentrations to suspensions of live cells and injured cells of the microorganism as an object of detection, leaving them for various periods of time, then irradiating them with visible light, harvesting the cells by centrifugation or the like as required, staining the cells with a nuclear stain agent, and analyzing the cells by FCM.

Preferred conditions for the irradiation of visible light can also be appropriately determined by performing such an experiment as mentioned above using various irradiation times. Specifically, the treatment with EMA is preferably performed with a final concentration of 0.5 to 100 µg/ml at a temperature of 4 to 10° C. for 5 minutes to 48 hours. Moreover, the EMA treatment is preferably performed under light shielding. As the visible light, visible lights containing 500 to 700 nm components are preferred. Specific examples of the conditions for the irradiation of visible light include irradiation of visible lights of 100 to 750 W for 5 minutes to 2 hours from a distance of 10 to 50 cm from the test sample. The irradiation of visible light is preferably performed at a low temperature, for example, with ice cooling of the sample.

(3) Step c)

In this step, the test sample treated in the steps a) and b) is treated with a nuclear stain agent. The nuclear stain agent contains at least a first stain agent that can penetrate cell walls of live cells, injured cells and dead cells. The expression "the stain agent can penetrate cell walls of live cells and dead cells" refers both the case where permeabilities of the agent for cell walls of live cells, injured cells and dead cells are substantially the same, and the case where, even if the permeabilities differ, difference of the permeabilities of the agent for cell walls of live cells and dead cells is smaller compared with that of the second stain agent described later. Specific examples of the first stain agent include, for example, SYTO9.

Moreover, the nuclear stain agent preferably further contains a second stain agent that is more likely to penetrate cell walls of dead cells than those of live cells and injured cells compared with the first stain agent. In other words, the second stain agent is a stain agent that can stain live cells and dead cells in different colors. Examples of the second stain agent include propidium iodide (PI). When these nuclear stain agents penetrate into the cells, they intercalate into chromosomal DNAs, and excited by irradiation of laser beams to emit fluorescence. For example, if SYTO9 and PI intercalating into DNA are irradiated with a laser beam of $\lambda$488 nm, they come to be in an excited state, and SYTO9 and PI emit green fluorescence with a center wavelength of $\lambda$518 nm, and red fluorescence with a center wavelength of $\lambda$617 nm, respectively.

In the staining with the stain agent, if there is a definite difference between live cells, and dead cells and somatic cells other than the microorganism existing in the test sample, the live cells can be distinguished to some extent using such a stain agent. However, even a stain agent that can penetrate into physically damaged dead cells may not penetrate into slightly injured cells, and thus show little difference in staining compared with live cells. In such a case, it is difficult to definitely distinguish live cells and injured cells only with the second stain agent.

However, chromosomal DNAs of injured cells are fragmented by the treatment of the step b) mentioned above, and thereby become more unlikely to stain with the stain agent, and therefore it becomes possible to distinguish live cells from injured cells and so forth by staining with the first stain agent. Furthermore, by using the second stain agent, two dimensional detection of the cells by FCM becomes possible. Therefore, in the present invention, although live cells can be detected only by staining with the first stain agent, use of the second stain agent enables distinction of live cells and dead cells to enhance detection accuracy, and therefore it is preferable to use both the first stain agent and the second stain agent.

Staining with the first stain agent and second stain agent may be performed by simultaneously using them, or separately using them.

Conditions for the staining with the stain agents are not particularly limited, and the conditions usually used for staining of chromosomal DNAs of microorganisms can be used. Specifically, it is preferable to add the stain agents to a cell suspension at a final concentration of 4.0 to 6.0 $\mu$M in the case of SYTO9, or 25.0 to 35.0 $\mu$M in the case of PI, and allow the reaction at 15 to 25° C. for 10 to 20 minutes.

(4) Step d)

In this step, the microorganism in the test sample treated with the nuclear stain agent in the step c) mentioned above is detected by FCM. The principle of the detection of microorganism by FCM is as follows.

If particles such as microorganism are arranged in line and irradiated with argon laser beam (1488 nm) in order, the light is be scattered at a small angle of 1.5 to 19° to the axis of the laser beam. This scattered light is called forward scattered light (FSC), and the scattering degree is substantially proportional to the size of particles. The light simultaneously scattered at an angle of about 90° to the axis of the laser beam is called side scattered light (SSC), and it is said to reflect the complexity of the internal structure of particles including DNA structure. Therefore, if a FSC-SSC plot is prepared as an x-y plot, the horizontal axis represents size of particles, and the vertical axis represents complexity of the internal structure of particles.

If bacteria are stained with the first nuclear stain agent and the second nuclear stain agent mentioned above, and irradiated with a laser beam, plotted points for individual cells locate in a certain specific region on a FSC-SSC plot. By surrounding the specific region on the plot with four sides (gate) using FCM analysis software (for example, Cell Quest Ver. 3.1, Becton Dickinson, Sydney, Australia), selectively retrieving only the particles of the bacterial region, and focusing only on the retrieved particles, dot plots of live cells and dead cells can be created (refer to FIGS. 1 to 8).

The FCM measurement is preferably performed with the following conditions. That is, it is preferable to use 15 mW argon laser beam (wavelength $\lambda$=488 nm) for excitation light, and measure the forward scattered light (FSC, <15°), side scattered light (>15°), and three kinds of fluorescence signals FL1 to 3, respectively. For the measurement of the fluorescence signals FL1 to 3, a band pass filter for 515 to 545 nm, especially 530 nm, is preferably used for green fluorescence (FL1), a band pass filter for 564 to 606 nm, especially 585 nm, is preferably used for yellow orange fluorescence (FL2), and a long wavelength band pass filter for 655 to 800 nm, especially 670 nm, is preferably used for red fluorescence (FL3).

Furthermore, the measurement is preferably performed with settings for detectors of FSC: E02, SSC: 376, FL1: 709, FL2: 736, and FL3: 811 (all are represented by using logarithmic gain), settings for % compensation of FL1-FL2: 0.0, FL2-FL1: 0.0, FL2-FL3: 0.0, and FL3-FL2: 0.0, FSC signal 150% of Threshold (boundary value), feeding rate of FCM test suspension of low flow rate: 12 $\mu$l/min, count of cells taken up into the gate on the FSC-SSC plot (particle number) of 5,000,000, and measurement time of 30 seconds.

For example, under the preferred conditions, live cells and injured cells are plotted in the SYTO9 positive and PI negative region (SYTO9(+)·PI(−)), and dead cells are mainly plotted in the SYTO9 positive and PI positive region (SYTO9(+)·PI(+)) on the SYTO9/PI plot. The boundary for negativity and positivity for SYTO9, and the boundary for negativity and positivity for PI are represented by a fluorescence intensity of $10^3$ in the case of SYTO9, and a fluorescence intensity of $2 \times 10^2$ in the case of PI. The settings of the gate are preferably FSC: $10^2$ to $2 \times 10^3$ and SSC: 10 to $2 \times 10^2$.

The analysis by FCM can be performed by using a commercially available FCM apparatus. Conditions for FCM are not particularly limited, and the conditions usually used for detection and separation of microorganisms such as bacteria can be used for the present invention.

In the present invention, the "detection of live cells" includes both determination of presence or absence of live cells in a test sample and determination of amount of live cells in a test sample. Moreover, the "detection of live cells" includes distinction of live cells from injured cells and/or dead cells, and determination of presence or absence of each of live cells, injured cells and dead cells. The amount of live cells is not limited to an absolute amount, and may be a relative amount with respect to that in a control sample.

<3>Kit of the Present Inventions

The first kit of the present invention is a kit for preparing the aforementioned first sample for FCM measurement comprising an enzyme selected from lipolytic enzymes and proteases as an element constituting the enzyme, a topoisomerase poison and/or a DNA gyrase poison, and a nuclear stain agent.

The second kit of the present invention is a kit for preparing the aforementioned second sample for FCM measurement comprising an enzyme selected from lipolytic enzymes and proteases as an element constituting the enzyme, ethidium monoazide, and a nuclear stain agent.

In the aforementioned kits, the enzyme selected from lipolytic enzymes and proteases, the topoisomerase poison and/or the DNA gyrase poison, and the nuclear stain agent are the same as those explained for the methods of the present invention.

The kits of the present invention can also comprise a diluent, an instruction describing the method of the present invention and so forth, besides the aforementioned elements.

EXAMPLES

Hereafter, the present invention will be more specifically explained with reference to the following examples. However, the present invention is not limited to the following examples.

[Test Samples]

In the following examples and control examples, experiments were performed by using test samples prepared by subjected to following treatments by using *Escherichia coli* DH5α (henceforth also simply referred to as "*Escherichia coli*") and *Staphylococcus epidermidis* KD strain (henceforth also simply referred to as "*Staphylococcus epidermidis*").

(1) Live cells and injured cells in a physiological saline suspension were detected by using a flow cytometer (referred to as the "untreated group").

(2) A physiological saline suspension of live cells and injured cells was treated with lipase and proteinase K, and then cells were detected by using a flow cytometer (referred to as the "LP-treated group"). The results of the samples of (1) and (2) mentioned above are shown in Control Example 1.

(3) Live cells and injured cells were suspended in cow's milk subjected to ultra high temperature pasteurization (130° C., 2 seconds, referred to as "UHT"), and cow's milk subjected to low temperature long time pasteurization (63° C., 30 minutes, referred to as "LTLT"), and the suspensions were treated with lipase and proteinase K. The cells in the suspensions were detected by using a flow cytometer (referred to as the "M-LP-treated group"). Moreover, the cells in cow's milk treated with lipase and proteinase K were detected by using a flow cytometer. The results are shown in Control Examples 2 and 3.

(4) The sample of (2) mentioned above was further subjected to an ethidium monoazide (EMA) treatment, and the cells therein were detected by using a flow cytometer (referred to as the "LPE-treated group"). The results are shown in Example 1.

(5) The sample of (3) mentioned above was further subjected to the EMA treatment, and the cells therein were detected by using a flow cytometer (referred to as the "M-LPE-treated group"). The results are shown in Examples 2 and 3.

(6) A sample was obtained in the same manner as that of (5) mentioned above provided that the EMA treatment was replaced with a treatment with a topoisomerase poison or a treatment with a DNA gyrase poison (referred to as the "M-LPD-treated group"). The results are shown in Example 4.

Control Example 1

Detection of Live Cells and Injured Cells of *Escherichia Coli* and *Staphylococcus epidermidis* Suspended in Physiological Saline (LP-Treated or Untreated) with Flow Cytometer (1) Preparation of Samples 1-1. Preparation of Suspensions of Live Cells and Injured Cells 1-1-1. *Escherichia Coli* Suspensions

*Escherichia coli* DH5α was inoculated into L broth, and cultured at 10° C. for 12 hours as stationary culture, and then the culture was subjected to refrigerated centrifugation at 4° C. and 3,000×g for 10 minutes to harvest the cells. The harvested cells were suspended in physiological saline (Otsuka Pharmaceutical, the same shall apply to the following description), and the suspension was centrifuged to harvest the cells again. The same procedure was repeated once more to wash the cells.

The washed cells were suspended in physiological saline, the suspension was appropriately diluted, and 0.1 ml of the suspension was applied on L agar medium and cultured to measure live cells count. The aforementioned cell suspension was finally adjusted at $4 \times 10^6$ cfu/ml to obtain a live cell suspension.

The live cell suspension in a volume of 1 ml was put into a 2 ml volume microtube, and immersed in boiling water at 100° C. for 50 seconds to prepare an injured cell suspension. Separately, another injured cell suspension was prepared, and applied in a volume of 0.1 ml on L agar medium to confirm that the cells did not form colonies.

1-1-2. *Staphylococcus Epidermidis* Suspensions

*Staphylococcus epidermidis* KD strain was inoculated into L broth, and cultured at 37° C. for 18 hours as stationary culture, and then the culture was subjected to refrigerated centrifugation at 4° C. and 3,000×g for 10 minutes to harvest the cells. The harvested cells were suspended in physiological saline (Otsuka Pharmaceutical), and the suspension was centrifuged to harvest the cells again. The same procedure was repeated once more to wash the cells. The washed cells were suspended in physiological saline, the suspension was appropriately diluted, 0.1 ml of the suspension was applied on L agar medium, and the cells were cultured to measure live cells count. The aforementioned cell suspension was finally adjusted at $4 \times 10^7$ cfu/ml to obtain a live cell suspension.

The live cell suspension in a volume of 1 ml was put into a 2 ml volume microtube, and the microtube was immersed in boiling water at 100° C. for 50 seconds to prepare an injured cell suspension. Separately, another injured cell suspension was prepared, and applied in a volume of 0.1 ml on L agar medium to confirm that the cells did not form colonies.

1-2. Lipase Treatment of and Proteinase K Treatment of Live Cell and Injured Cell Suspensions Each of the *Escherichia coli* suspensions (live cells and injured cells) and the *Staphylococcus epidermidis* suspensions (live cells and injured cells) prepared in 1-1-1 and 1-1-2 mentioned above in a volume of 1 ml was put into a 2 ml volume microtube. The suspension was added 100 μl of lipase (E.C. 3.1.1.3, Sigma) adjusted at 189 U/ml with physiological saline, and the suspension was incubated at 37° C. for 30 minutes to perform a lipase treatment.

To each cell suspension subjected to the lipase treatment, 20 μl of a 1250 U/ml proteinase K (E.C. 3.4.21.64, Sigma) solution was added, and the mixture was incubated at 37° C. for 30 minutes to perform a proteinase K treatment.

After the lipase treatment and the proteinase K treatment (henceforth also referred to as "LP treatment"), the cells were harvested by refrigerated centrifugation at 4° C. and 14,000×g for 10 minutes, and the harvested cells were suspended in physiological saline to prepare LP-treated group *Escherichia coli* suspensions (live cells and injured cells) and LP-treated group *Staphylococcus epidermidis* suspensions (live cells and injured cells), respectively.

In addition, in the aforementioned method, 100 μl of physiological saline was added instead of the lipase, and 20 μl of physiological saline was added instead of proteinase K, and treated in the same way to prepare untreated group *Escherichia coli* suspensions (live cells and injured cells) and untreated group *Staphylococcus epidermidis* suspensions (live cells and injured cells), respectively.

(2) Method of FCM Test

To each of the LP-treated group *Escherichia coli* suspensions (live cells and injured cells), the LP-treated group *Staphylococcus epidermidis* suspensions (live cells and injured cells), the untreated group *Escherichia coli* suspensions (live cells and injured cells) and the untreated group *Staphylococcus epidermidis* suspensions (live cells and injured cells) taken in a volume of 300 μl, 0.9 μl of an SYTO9/PI fluorescence staining reagent (LIVE/DEAD BacLight™ Bacterial Viability kit, Molecular Probes, SYTO9/PI=1/1 mixture) was added, and the reaction was allowed at room temperature for 15 minutes under light shielding to prepare each sample. For these samples, measurement was performed by using an FCM measurement apparatus, FACS Calibur (Becton Dickinson).

The measurement conditions were as follows. As the excitation light was used 15 mW argon laser light (wavelength λ=488 nm), and as the sheath solution for feeding FCM sample liquid, Becton Dickinson product was used. Further, the forward scattered light (FSC, <15°), side scattered light (>15°), and three kinds of fluorescence signals FL1 to 3 were measured, respectively. For the measurement of the fluorescence signals FL1 to FL3, a band pass filter for 530 nm (515 to 545 nm) was used for green fluorescence (FL1), a band pass filter for 585 nm (564 to 606 nm) was used for yellow orange fluorescence (FL2), and a long wavelength band pass filter for 670 nm (655 to 800 nm) was used for red fluorescence (FL3).

The settings of detectors FSC: E02, SSC: 376, FL1: 709, FL2: 736, and FL3: 811 (all are represented by using logarithmic gain), and settings of % compensation FL1-FL2: 0.0, FL2-FL1: 0.0, FL2-FL3: 0.0, and FL3-FL2: 0.0 were used, FSC signal 150 was set to Threshold (boundary value), feeding rate of FCM test suspension was set to 12 μl/min, count of cells taken up into the gate on the FSC-SSC plot (particle number) was set to 5,000,000, and measurement time was set to 30 seconds, respectively, to perform the measurement.

(3) Test Results

The results of this test are shown in FIG. 1.

SYTO9 shows high cell wall permeability and penetrates cell walls of live cells and dead cells, whereas PI shows low cell wall permeability and penetrates only cell walls of physically injured dead cells. Therefore, originally, the results of live cells should be plotted in the region of SYTO9(+)·PI(−), and those of dead cells should be plotted in the region of SYTO9(+)·PI(+) on a SYTO9/PI plot. Actually, when the results of the untreated group *Escherichia coli* suspensions (live cells and injured cells) and the untreated group *Staphylococcus epidermidis* suspensions (live cells and injured cells) were compared, PI did not penetrate into not only live cells but also injured cells, and live cells and injured cells could not be clearly distinguished. Therefore, it is estimated that injury degree of cell walls of bacteria after immersion in boiling water at 100° C. for 50 seconds, conditions similar to those of ultrahigh temperature sterilization (commercial cow's milk), is not significant. Moreover, there was a small difference in the fluorescence intensity observed in SYTO9 staining between live cells and injured cells, and it is estimated that this difference was caused because chromosomal DNAs of injured cells were partially decomposed by heating, and thus efficiency of intercalation of SYTO9 into the chromosomal DNAs was lowered.

Even if the LP treatment was performed, live cells and injured cells could not be clearly distinguished in the case of, in particular, *Escherichia coli*. When the results of the untreated group *Escherichia coli* suspension (live cells) and the LP-treated group *Escherichia coli* suspension (live cells) are compared, it can be seen that a part of the points plotted in the SYTO9(+)'PI(−) region moved to the SYTO9(−)·PI(−) region on the plot of live *Escherichia coli*, and detection efficiency of live cells decreased, because the LP treatment was performed. This phenomenon is more marked compared with the case of *Staphylococcus epidermidis*. However, when live cells and injured cells were separately detected from cow's milk by FCM, the contaminants, i.e., somatic cells such as bovine leucocytes and mammary epitheliocytes, micellar casein and lipids must be eliminated, and thus it is considered that the LP treatment is inevitable.

Control Example 2

Detection of *Escherichia coli* Live Cells (LP-Treated) Suspended in Homogenized Milk Subjected to Ultra High Temperature Pasteurization with Flow Cytometer (1) Preparation of Samples To 1 ml of 1.1×10$^7$ cfu/ml *Escherichia coli* suspension (live cells) prepared in the same manner as that in Control Example 1, 9 ml of commercial homogenized cow's milk (subjected to ultra high temperature pasteurization (130° C., 2 seconds) henceforth also referred to as the "UHT homogenized milk") was added to dilute the suspension 10 times, and the diluted suspension was serially diluted in the same manner to prepare UHT homogenized milk inoculated with 1.1×10$^2$ to 1.1×10$^6$ cfu/ml *Escherichia coli* (live cells). As the aforementioned UHT homogenized milk, one confirmed not to form colonies when it was incubated at 37° C. for 48 hours and at 25° C. for 72 hours on an agar medium was used.

Then, the UHT homogenized milk of various dilution rates inoculated with *Escherichia coli* (live cells) and the UHT homogenized milk not inoculated with *Escherichia coli* were subjected to the same lipase treatment and proteinase K treatment (LP treatment) as those of Control Example 1. That is, each of the UHT homogenized milk inoculated with *Escherichia coli* (live cells) and UHT homogenized milk not inoculated with *Escherichia coli* in a volume of 1 ml was put into a 2 ml volume microtube. The sample was added 100 μl of lipase (E.C. 3.1.1.3, Sigma) adjusted at 189 U/ml with physiological saline, and the mixture was incubated at 37° C. for 30 minutes to perform a lipase treatment.

To each sample subjected to the lipase treatment, 20 μl of a 1250 U/ml proteinase K (E.C. 3.4.21.64, Sigma) solution was added, and the mixture was incubated at 37° C. for 30 minutes to perform a proteinase K treatment.

After the lipase treatment and the proteinase K treatment, 880 μl of physiological saline was added to each sample, and the sample was subjected to refrigerated centrifugation at 4° C. and 14,000×g for 10 minutes. The lipid layer existing in the upper layer was completely removed with a swab, and the aqueous layer existing in the middle layer was also removed. 2 ml of physiological saline was added to the remained lower layer, the mixture was subjected to refrigerated centrifugation at 4° C. and 14,000×g for 10 minutes for washing, the pellet was collected, and 300 μl of physiological saline was added to the pellet.

(2) Test Method

To each of the LP-treated UHT homogenized milk inoculated with the *Escherichia coli* (live cells) and LP-treated UHT homogenized milk prepared above and taken in a volume of 300 μl, 0.9 μl of the SYTO9/PI fluorescence staining reagent was added, and the reaction was allowed at room temperature for 15 minutes under light shielding to prepare each sample. For these samples, measurement was performed by using an FCM measurement apparatus, FACS Calibur (Becton Dickinson). The measurement conditions were the same as those of Control Example 1, except that the measurement time was 5 minutes.

(3) Test Results

The results of the test are shown in FIG. 2.

Although the number of plotted points in the SYTO9(+)·PI(−) region varied depending on the concentration of inoculated *Escherichia coli* (live cells), there were many plotted points in this region even in the case of the LP-treated UHT homogenized milk not inoculated with *Escherichia coli* (live cells), and distinction from *Escherichia coli* (live cells) was difficult. It is considered that these contaminants consisted of somatic cells and cells originally contained in the cow's milk and injured by heat. It is considered that, however, because cell membranes of the former and cell walls of the latter are not damaged so significantly by ultrahigh temperature sterilization, SYTO9 penetrated into the cells, but PI did not penetrate into them. As reference, the results obtained by subtracting the number of plotted points in the SYTO 9(+)'PI(−) region for the LP-treated UHT homogenized milk not inoculated with *Escherichia coli* (live cells) from each number of plotted points in the same region for the LP-treated UHT homogenized milk inoculated with *Escherichia coli* (live cells) are shown in Table 1. According to the results, it is considered that the detection limit of *Escherichia coli* (live cells) is $1.1 \times 10^4$ cfu/ml under the conditions of this test.

TABLE 1

Results of detection of live *Escherichia coli* in LP-treated UHT homogenized milk

| Number of inoculated bacteria (cfu/ml) | FCM count (actually measured value) |
| --- | --- |
| 0 | 0 |
| $1.1 \times 10^2$ | 0 |
| $1.1 \times 10^3$ | 0 |
| $1.1 \times 10^4$ | 311 |
| $1.1 \times 10^5$ | 2755 |
| $1.1 \times 10^6$ | 128457 |

Control Example 3

Detection of Live Cells and Injured Cells of *Escherichia Coli* and *Staphylococcus epidermidis* (LP-Treated) Suspended in Non-Homogenized Milk Subjected to Low Temperature Long Time Pasteurization (LTLT) with Flow Cytometer (1) Preparation of Samples To 1 ml each of $1.5 \times 10^7$ cfu/ml *Escherichia coli* suspensions (live cells and injured cells) prepared in the same manner as that in Control Example 1, 9 ml of commercial cow's milk not subjected to a homogenization treatment (non-homogenized, subjected to low temperature long time pasteurization (63° C., 30 minutes), henceforth also referred to as the "LTLT non-homogenized milk") was added to dilute the suspensions 10 times, and diluted suspensions were serially diluted in the same manner to prepare LTLT non-homogenized milk inoculated with $1.5 \times 10^2$ to $1.5 \times 10^6$ cfu/ml *Escherichia coli* (live cells and injured cells). As the aforementioned LTLT non-homogenized milk, one confirmed not to form colonies when it was incubated at 37° C. for 48 hours and at 25° C. for 72 hours on an agar medium was used.

Further, to 1 ml each of $1.8 \times 10^8$ cfu/ml *Staphylococcus epidermidis* suspensions (live cells and injured cells) prepared in the same manner as that in Control Example 1, 9 ml of LTLT non-homogenized cow's milk was added to dilute the suspensions 10 times, and the diluted suspensions were serially diluted in the same manner to prepare LTLT non-homogenized milk inoculated with $1.8 \times 10^2$ to $1.8 \times 10^7$ cfu/ml *Staphylococcus epidermidis* (live cells and injured cells).

Then, the LTLT non-homogenized milk inoculated with *Escherichia coli* (live cells and injured cells) of various dilution rates, the LTLT non-homogenized milk inoculated with *Staphylococcus epidermidis* (live cells and injured cells) of various dilution rates, and the LTLT non-homogenized milk not inoculated with the bacteria were subjected to the same lipase treatment and proteinase K treatment (LP treatment) as those of Control Example 1. That is, each of the LTLT non-homogenized milk inoculated with *Escherichia coli* (live cells and injured cells), the LTLT non-homogenized milk with *Staphylococcus epidermidis* (live cells and injured cells), and the LTLT non-homogenized milk not inoculated with the bacteria in a volume of 1 ml was put into a 2 ml volume microtube. The sample was added 100 μl of lipase (E.C. 3.1.1.3, Sigma) adjusted at 189 U/ml with physiological saline, and the sample was incubated at 37° C. for 30 minutes to perform a lipase treatment.

To each sample subjected to the lipase treatment, 20 μl of a 1250 U/ml proteinase K (E.C. 3.4.21.64, Sigma) solution was added, and the sample was incubated at 37° C. for 30 minutes to perform a proteinase K treatment.

After the lipase treatment and the proteinase K treatment, 880 μl of physiological saline was added to each sample, and the sample was subjected to refrigerated centrifugation at 4° C. and 14,000×g for 10 minutes. The lipid layer existing in the upper layer was completely removed with a swab, and the aqueous layer existing in the middle layer was also removed. 2 ml of physiological saline was added to the remained lower layer, the mixture was subjected to refrigerated centrifugation at 4° C. and 14,000×g for 10 minutes for washing, the pellet was collected, and 300 μl of physiological saline was added to the pellet.

(2) Test Method

To each of the LP-treated LTLT non-homogenized milk inoculated with *Escherichia coli* (live cells and injured cells), the LP-treated LTLT non-homogenized milk inoculated with *Staphylococcus epidermidis* (live cells and injured cells), and the LP-treated LTLT non-homogenized milk not inoculated with the bacteria prepared above and taken in a volume of 300 μl, 0.9 μl of an SYTO9/PI fluorescence staining reagent was added, and the reaction was allowed at room temperature for 15 minutes under light shielding to prepare each sample. For these samples, measurement was performed by using an FCM measurement apparatus, FACS Calibur (Becton Dickinson). The measurement conditions were the same as those of Control Example 1, except that the measurement time was 5 minutes.

(3) Test Results

The results of this test are shown in FIG. 3.

There were many plotted points in the SYTO9(+)·PI(−) region for the LP-treated LTLT non-homogenized milk not inoculated with the bacteria, and they degraded the detection limits for *Escherichia coli* (live cells) and *Staphylococcus epidermidis* (live cells). The plotted points for *Escherichia coli* (injured cells) and *Staphylococcus epidermidis* (injured cells) were hidden by plotted points originating in the LP-treated LTLT non-homogenized milk not inoculated with the bacteria.

Because the LTLT non-homogenized milk originally contained injured cells and dead cells at a concentration of $10^3$ to $10^5$ cfu/ml, it is highly possible that the plotted points of the injured cells newly inoculated in Control Example 3 would be hidden by those of the originally contained cells. In addition, also in view of the locations of the plotted points for the LP-treated *Escherichia coli* and *Staphylococcus epidermidis* (injured cells) suspensions, which are seen from the results of Control Example 1 shown in FIG. 1, it is considered to be highly possible that the plotted points of the newly inoculated injured cells would be hidden by those originating in the LP-treated LTLT non-homogenized milk.

The numbers of plotted points in the SYTO9(+)·PI(−) plotting region satisfying the condition that SYTO9 intensity $\geq 7 \times 10^3$ are shown in Table 2 for the LP-treated LTLT non-homogenized milk inoculated with *Escherichia coli* (live cells) and the LP-treated LTLT non-homogenized milk. It is considered that the detection limit of LP-treated method for *Escherichia coli* (live cells) in the LP-treated LTLT non-homogenized milk is $1.5 \times 10^5$ cfu/ml under the conditions of this test.

TABLE 2

Results of detection of live *Escherichia coli* in LP-treated LTLT non-homogenized milk by LP-treated method

| Number of inoculated bacteria (cfu/ml) | FCM count (actually measured value)[1] |
|---|---|
| 0 | 9 |
| $1.5 \times 10^2$ | 8 |
| $1.5 \times 10^3$ | 10 |
| $1.5 \times 10^4$ | 9 |
| $1.5 \times 10^5$ | 18 |
| $1.5 \times 10^6$ | 111 |

[1] The numbers of plotted points in the SYTO9(+) •PI(−) plotting region satisfying the condition that SYTO9 intensity $\geq 7 \times 10^3$ were counted.

Further, the numbers of plotted points in the SYTO9(+)·PI(−) plotting region satisfying the condition that SYTO9 intensity $\geq 7 \times 10^3$ are shown in Table 3 for the LP-treated LTLT non-homogenized milk inoculated with *Staphylococcus epidermidis* (live cells) and the LP-treated LTLT non-homogenized milk. It is considered that the detection limit of LP-treated method for *Staphylococcus epidermidis* (live cells) in the LP-treated LTLT non-homogenized milk is $1.8 \times 10^6$ cfu/ml under the conditions of this test.

TABLE 3

Results of detection of live *Staphylococcus epidermidis* in LTLT non-homogenized milk by LP-treated method.

| Number of inoculated bacteria (cfu/ml) | FCM count (actually measured value)[1] |
|---|---|
| 0 | 9 |
| $1.8 \times 10^2$ | 8 |
| $1.8 \times 10^3$ | 10 |
| $1.8 \times 10^4$ | 8 |
| $1.8 \times 10^5$ | 7 |
| $1.8 \times 10^6$ | 47 |
| $1.8 \times 10^7$ | 296 |

[1] The numbers of plotted points in the SYTO9(+) •PI(−) plotting region satisfying the condition that SYTO9 intensity $\geq 7 \times 10^3$ were counted.

Example 1

Detection in ethidium monoazide (EMA) treated *Escherichia coli* suspension and *Staphylococcus epidermidis* suspension (LP-treated) by using flow cytometer.

(1) Preparation of Samples

Each of *Escherichia coli* suspensions (live cells and injured cells, $4 \times 10^6$ cfu/ml) and *Staphylococcus epidermidis* suspensions (live cells and injured cells, $4 \times 10^7$ cfu/ml) prepared in the same manner as that in Control Example 1 in a volume of 1 ml was put into a 2 ml volume microtube, and subjected to a lipase treatment and proteinase K treatment (LP treatment) in the same manner as that in Control Example 1 and then refrigerated centrifugation at 4° C. and 14,000×g for 10 minutes. After the upper aqueous layer was removed, 1 ml of physiological saline was added to the cells of the lower layer (precipitates) to suspend the cells.

Ethidium monoazide (henceforth also abbreviated as "EMA", Sigma, catalog number: E2028) was dissolved in sterilized water at a concentration of 1000 µg/ml, and filtered through a 0.45 µm microfilter. This EMA aqueous solution in a volume of 10 µl was added to the aforementioned LP-treated cell suspension, and the suspension was left at 4° C. for 30 minutes under light shielding. Then, the suspension was put on ice, and irradiated with visible light from a lamp of 500 W (FLOOD PRF, 100 V, 500 W, Iwasaki Electric Co., Ltd.) disposed at a distance of 20 cm from the suspension for 10 minutes. The above procedure of adding the EMA solution and irradiating visible light is also referred to as the "EMA treatment". Then, 990 µl of physiological saline was added to the suspension, and the suspension was subjected to refrigerated centrifugation at 4° C. and 14,000×g for 10 minutes. After the upper aqueous layer was removed, 300 µl of physiological saline was added to the pellet of the lower layer, then 0.9 µl of an SYTO9/PI fluorescence staining reagent was added to the mixture, and the reaction was allowed at room temperature for 15 minutes under light shielding to prepare each sample.

(2) Test Method

FCM measurement was performed for each of the samples prepared above (measurement time: 30 seconds) in the same manner as that in Control Example 1.

(3) Test Results

The results of this test are shown in FIG. 4.

As shown in FIG. 1 referred to above, the live cells and injured cells of *Escherichia coli* could not be clearly distinguished, when only the LP treatment was performed. However, as clearly seen from the results of this test, when the EMA treatment was performed after the LP treatment, it became possible to clearly distinguish live cells and injured cells of *Escherichia coli*. In addition, the same results were also obtained for *Staphylococcus epidermidis*. It is considered that this was because EMA showing low cell wall permeability did not penetrate cell walls of live cells, but penetrated cell walls of injured cells of which damage was not so significant.

EMA having penetrated into injured cells disorderly intercalates into chromosomal DNAs in the cells of the injured bacteria, then converted into nitrene by irradiation of visible light, and binds to the chromosomal DNAs by covalent attachment. Because the DNA gyrase or topoisomerase activity remains in the cells after short time pasteurization, rewinding of DNA strands occurs for transcription of genes during metabolism, and thus cleavage and religation of chromosomal DNAs occur. At the time of the religation, the religation of DNAs by the aforementioned enzymes is inhibited by the action of covalent attachment of nitrene originated in EMA, and as a result, fragmentation of chromosomal DNAs is promoted. When SYTO9 is allowed to act on injured cells containing fragmented chromosomal DNAs, the fluorescence intensity thereof clearly decreases as compared with that observed before the EMA treatment. It is considered that this is because the fragmentation of DNA reduces efficiency of intercalation of SYTO9 into DNA. However, since EMA cannot penetrate cell walls of live cells, chromosomal DNAs of live cells are not affected. Therefore, it is considered that even if the EMA treatment is performed, live cells do not show change of fluorescence intensity obtained by SYTO9.

Example 2

Detection of *Escherichia coli* and *Staphylococcus epidermidis* live cells (LP-treated) suspended in UHT homogenized milk treated with ethidium monoazide (EMA) by using flow cytometer (1) Preparation of Samples To 1 ml of $6\times10^7$ cfu/ml *Escherichia coli* suspension (live cells) prepared in the same manner as that in Control Example 1, 9 ml of the UHT homogenized milk used in Control Example 2 was added to dilute the suspension 10 times, and the diluted suspension was serially diluted in the same manner to prepare UHT homogenized milk inoculated with $6\times10^1$ to $6\times10^5$ cfu/ml *Escherichia coli* (live cells).

Further, to 1 ml of $1.9\times10^8$ cfu/ml *Staphylococcus epidermidis* suspension (live cells) prepared in the same manner as that in Control Example 1, 9 ml of the UHT homogenized milk was added to dilute the suspension 10 times, and the diluted suspension was serially diluted in the same manner to prepare UHT homogenized milk inoculated with $1.9\times10^2$ to $1.9\times10^7$ cfu/ml *Staphylococcus epidermidis* (live cells). Separately, UHT homogenized milk not inoculated with the bacteria was also prepared.

Each of the UHT homogenized milk inoculated with *Escherichia coli* (live cells), UHT homogenized milk inoculated with *Staphylococcus epidermidis* (live cells), and UHT homogenized milk not inoculated with the bacteria in a volume of 1 ml was put into a 2 ml volume microtube, and subjected to a lipase treatment and proteinase K treatment (LP treatment) in the same manner as that in Control Example 1. To the suspension, 880 µl of physiological saline was added, and the mixture was subjected to refrigerated centrifugation at 4° C. and 14,000×g for 10 minutes. The upper lipid layer was removed with a swab, and the aqueous layer as the middle layer was also removed. Then, 1 ml of physiological saline was added to the cells of the lower layer (precipitates) to suspend the cells. To each of the LP-treated cell suspensions and UHT homogenized milk not inoculated with bacteria, 10 µl of the 1000 µg/ml EMA aqueous solution used in Example 1 was added, and the mixture was left at 4° C. for 5 minutes under light shielding, and irradiated with visible light of 500 W on ice from a lamp (FLOOD PRF, 100 V, 500 W, Iwasaki Electric Co., Ltd.) for 5 minutes (EMA treatment). Then, 990 µl of physiological saline was added to the sample, and the sample was subjected to refrigerated centrifugation at 4° C. and 14,000×g for 10 minutes. After the upper aqueous layer was removed, 300 µl of physiological saline was added to the pellet of the lower layer, then 0.9 µl of a SYTO9/PI fluorescence staining reagent was added to the mixture, and the reaction was allowed at room temperature for 15 minutes under light shielding to prepare each sample.

(2) Test Method

FCM measurement was performed for each of the samples prepared above (measurement time: 5 minutes) in the same manner as that in Control Example 1.

(3) Test Results

Figure 5A:
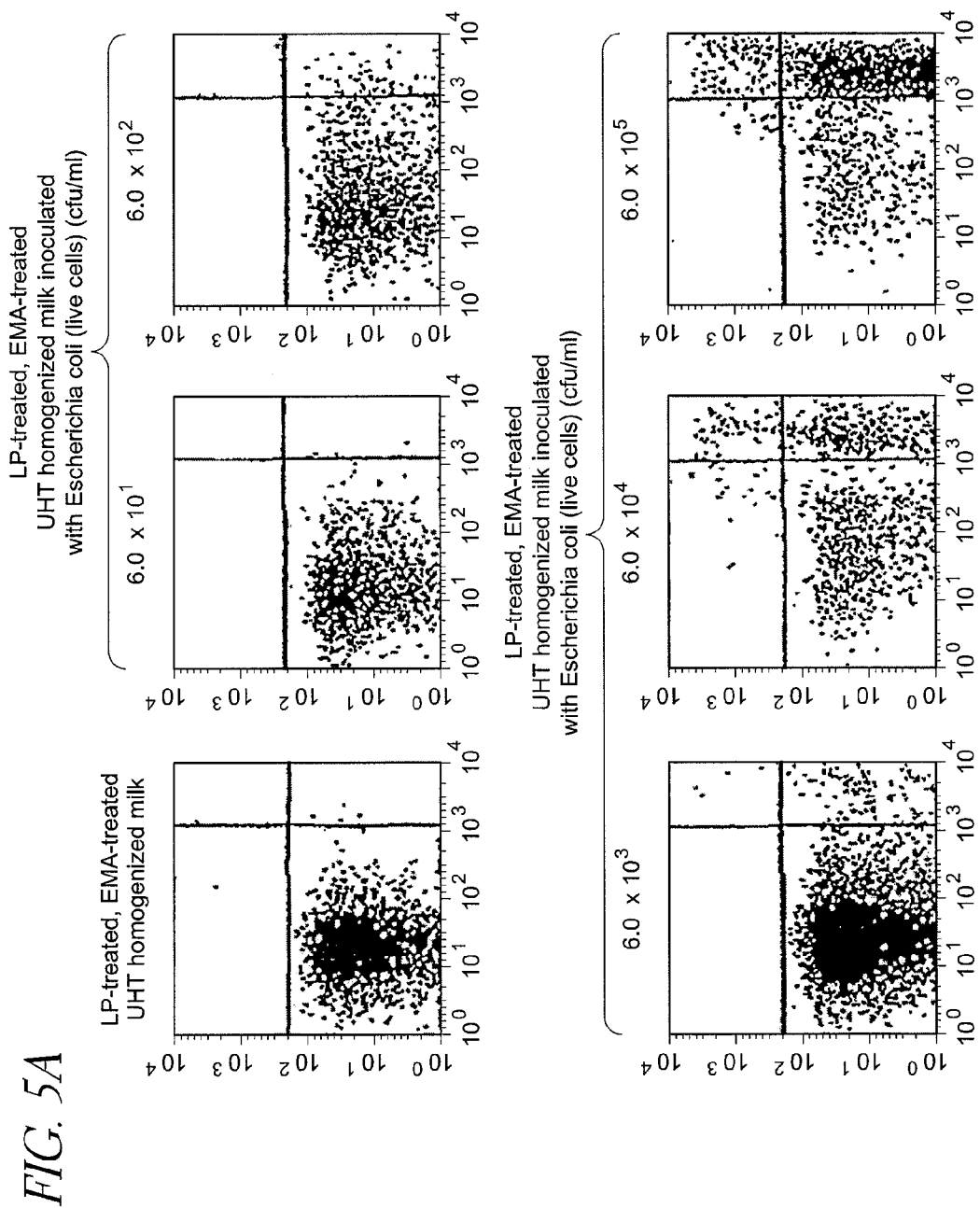
FIG. 5A shows LP-treated and EMA-treated UHT homogenized milk inoculated with *Escherichia coli* (live bacteria)
Figure 5B:
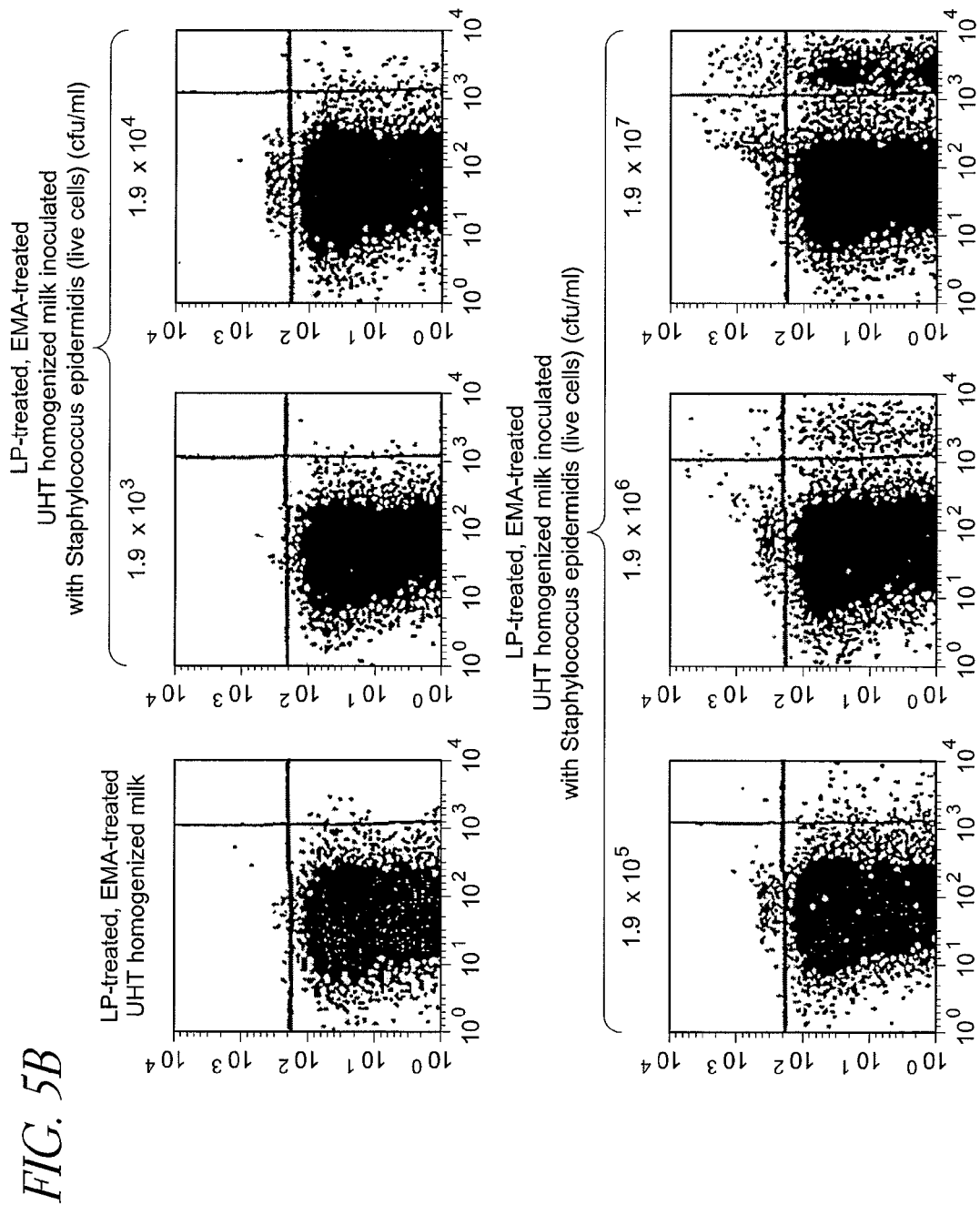
FIG. 5B shows UHT homogenized milk inoculated with *Staphylococcus epidermidis* (live bacteria). UHT homogenized milk not inoculated with the bacteria are indicated on the figure.

The results of this test are shown in FIG. 5. As shown in Control Example 2 mentioned above, in the results shown in FIG. 2, when live *Escherichia coli* was detected in the UHT homogenized milk by LP-treated method, a lot of plotted points for contaminants of somatic cells and injured cells were present in the SYTO9(+)·PI(−) region, which region represents presence of *Escherichia coli* (live cells), and as a result, the detection limit was as high as $1.1\times10^4$ cfu/ml.

However, as clearly seen from the results of this test, in the SYTO9/PI plot for the LP-treated and EMA-treated UHT homogenized milk not inoculated with *Escherichia coli*, the SYTO9 intensity was suppressed to $1\times10^1$ to $5\times10^1$, and the results were hardly plotted in the SYTO9(+)·PI(−) region representing presence of live cells.

Moreover, the number of plotted points in the SYTO9(+)·PI(−) region changed depending on the inoculation concentration of *Escherichia coli* (live cells). The numbers of plotted points in this region for each inoculation concentration are shown in Table 4. It is considered that the detection limit of *Escherichia coli* (live cells) in UHT homogenized milk subjected to the LP treatment and the EMA treatment (LPE treatment) is $6.0\times10^2$ cfu/ml under the conditions of this test.

TABLE 4

Results of detection of live *Escherichia coli* in UHT homogenized milk by LPE-treated method.

| Number of inoculated bacteria (cfu/ml) | FCM count (actually measured value) |
|---|---|
| 0 | 5 |
| $6.0 \times 10^1$ | 3 |
| $6.0 \times 10^2$ | 72 |
| $6.0 \times 10^3$ | 157 |
| $6.0 \times 10^4$ | 376 |
| $6.0 \times 10^5$ | 2316 |

Further, the aforementioned LP treatment and EMA treatment were performed in the same manner except that the volume of the sample used for the aforementioned LP treatment and EMA treatment was changed from 1 ml to 10 ml (concentrations of lipase, proteinase K and EMA were the same), and measurement was performed with a flow cytometer. The results of the measurement of the number of plotted points in the SYTO9(+)·PI(−) region are shown in Table 5. It is considered that the detection limit of *Escherichia coli* (live cells) in UHT homogenized milk is $6.0\times10^1$ cfu/ml under the conditions of this test. As compared with the detection limit obtained by using the LP treatment mentioned in Control Example 2, $1.1\times10^4$ cfu/ml, the detection limit for *Escherichia coli* (live cells) was improved to a concentration as low as about $1/(1.8\times10^2)$.

TABLE 5

Results of detection of live *Escherichia coli* in UHT homogenized milk by LPE-treated method (10 ml reaction scale)

| Number of inoculated bacteria (cfu/ml) | FCM count (actually measured value) |
|---|---|
| 0 | 1 |
| $6.0 \times 10^1$ | 14 |
| $6.0 \times 10^2$ | 113 |
| $6.0 \times 10^3$ | 506 |
| $6.0 \times 10^4$ | 4360 |
| $6.0 \times 10^5$ | 45541 |

The numbers of plotted points in the SYTO9(+)·PI(−) region counted for *Staphylococcus epidermidis* are shown in Table 6. According to the results, the detection limit for *Staphylococcus epidermidis* (live cells) in the UHT homogenized milk was $1.9\times10^4$ cfu/ml. The causes for the higher detection limit compared with that for *Escherichia coli* are considered the extremely strong tendency of *Staphylococcus epidermidis* to adsorb on the lipid layer formed in the middle of the LP treatment, and the marked decrease of the plotted points for LP-treated *Staphylococcus epidermidis* (live cells) in the SYTO9(+)·PI(−) region as the live cells region in contrast to the plotted points in the SYTO9(+)·PI(−) region observed for untreated *Staphylococcus epidermidis* (live cells), which corresponded to most of the cells.

TABLE 6

Results of detection of live *Staphylococcus epidermidis* in UHT homogenized milk by LPE-treated method

| Number of inoculated bacteria (cfu/ml) | FCM count (actually measured value) |
|---|---|
| 0 | 28 |
| $1.9 \times 10^2$ | 24 |
| $1.9 \times 10^3$ | 17 |
| $1.9 \times 10^4$ | 95 |
| $1.9 \times 10^5$ | 149 |
| $1.9 \times 10^6$ | 584 |
| $1.9 \times 10^7$ | 5263 |

Example 3

Detection of *Escherichia coli* and *Staphylococcus epidermidis* live cells and injured cells (LP-treated) suspended in LTLT non-homogenized milk treated with ethidium monoazide (EMA) by using flow cytometer (1) Preparation of Samples To 1 ml each of $1.5\times10^7$ cfu/ml *Escherichia coli* suspensions (live cells and injured cells) prepared in the same manner as that in Control Example 1, 9 ml of the LTLT non-homogenized milk used in Control Example 2 was added to dilute each suspension 10 times, and the diluted suspension was serially diluted in the same manner to prepare LTLT non-homogenized milk inoculated with $1.5\times10^2$ to $1.5\times10^6$ cfu/ml *Escherichia coli* (live cells and injured cells).

Further, to 1 ml each of $1.8\times10^8$ cfu/ml *Staphylococcus epidermidis* suspensions (live cells and injured cells) prepared in the same manner as that in Control Example 1, 9 ml of the LTLT non-homogenized milk used in Control Example 2 was added to dilute each suspension 10 times, and the diluted suspension was serially diluted in the same manner to prepare LTLT non-homogenized milk inoculated with $1.8\times10^2$ to $1.8\times10^7$ cfu/ml *Staphylococcus epidermidis* (live cells and injured cells). Separately, LTLT non-homogenized milk not inoculated with the bacteria was also prepared.

Each of the LTLT non-homogenized milk inoculated with *Escherichia coli* (live cells), LTLT non-homogenized milk inoculated with *Staphylococcus epidermidis* (live cells), and LTLT non-homogenized milk not inoculated with the bacteria was subjected to the same lipase treatment and proteinase K treatment (LP treatment) as well as EMA treatment as those in Example 2. Then, 990 µl of physiological saline was added to the sample, and the mixture was subjected to refrigerated centrifugation at 4° C. and 14,000×g for 10 minutes. After the upper aqueous layer was removed, 300 µl of physiological saline was added to the pellet of the lower layer, then 0.9 µl of an SYTO9/PI fluorescence staining reagent was added to the mixture, and the reaction was allowed at room temperature for 15 minutes under light shielding to prepare each sample.

(2) Test Method

FCM measurement was performed for each of the samples prepared above (measurement time: 5 minutes) in the same manner as that in Control Example 1.

(3) Test Results

Figure 6A:
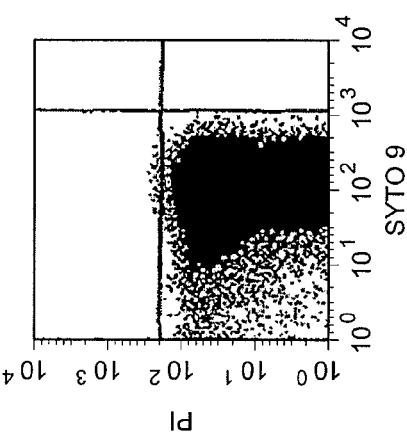
FIG. 6A shows results without bacterial inoculation.
Figure 6B:
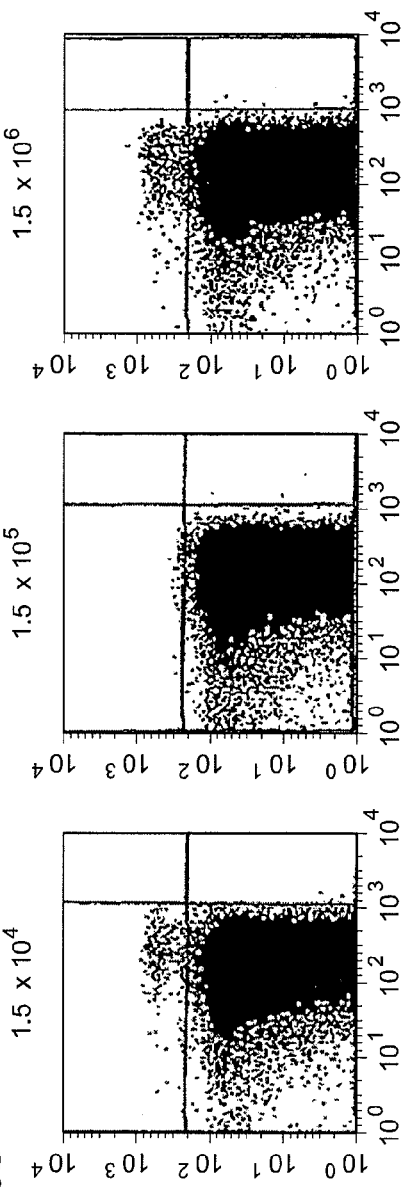
FIG. 6B shows results for injured cells.
Figure 6C:
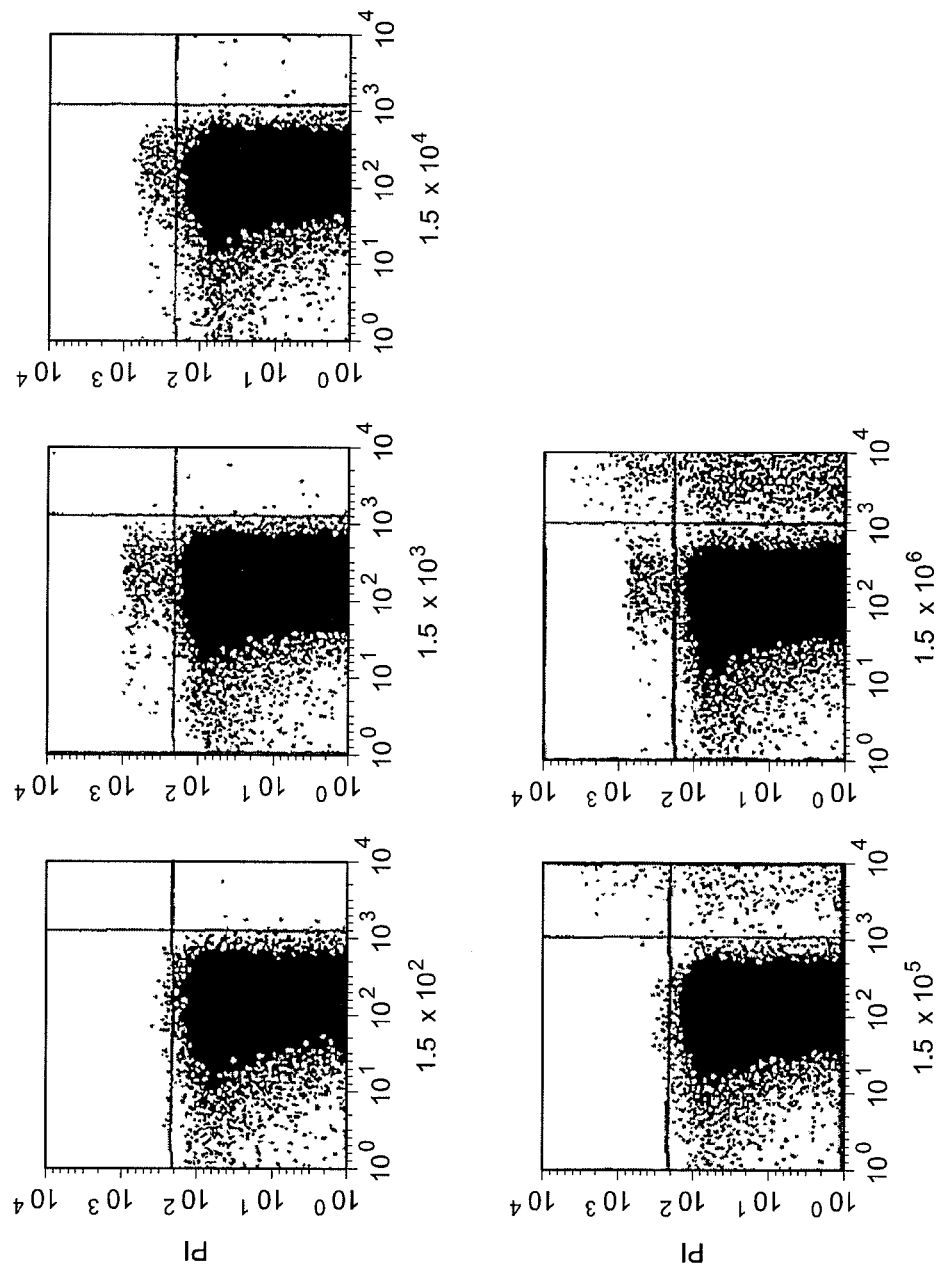
FIG. 6C shows results for live cells.
Figure 7B:
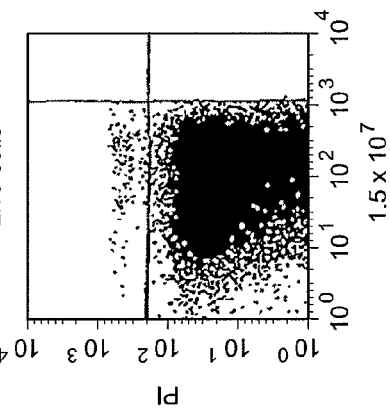
FIG. 7B shows LP-treated and EMA-treated LTLT non-homogenized milk inoculated with *Staphylococcus epidermidis* (live bacteria injured bacteria).
Figure 7A:
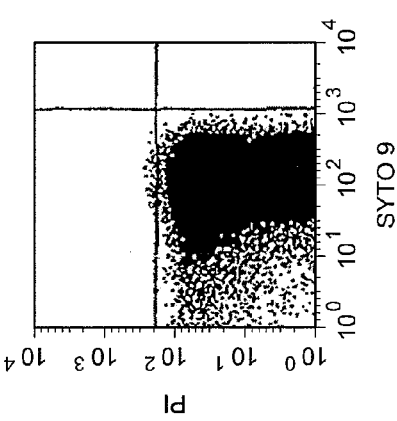
FIG. 7A shows results without bacterial inoculation.
Figure 7C:
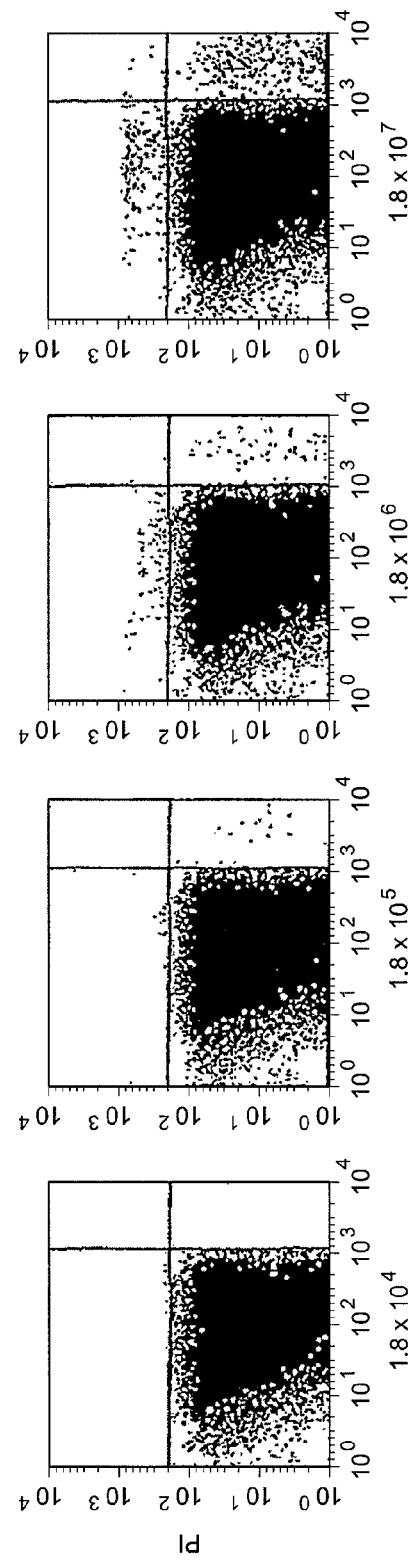
FIG. 7C shows LP-treated and EMA-treated LTLT non-homogenized milk inoculated with *Staphylococcus epidermidis* (live bacteria).

The results of this test are shown in FIGS. 6 and 7. As shown in Control Example 3 mentioned above, according to the results shown in FIG. 3, when live *Escherichia coli* and *Staphylococcus epidermidis* were detected in the LP-treated LTLT non-homogenized milk, a lot of plotted points for contaminants of somatic cells and injured cells were present in the SYTO9(+)·PI(−) region, whose region represents presence of *Escherichia coli* (live cells) and *Staphylococcus epidermidis* (live cells), as a result, the detection limit for *Escherichia coli* was $1.5\times10^5$ cfu/ml, and the detection limit for *Staphylococcus epidermidis* was $1.8\times10^6$ cfu/ml, both of which are at high level.

However, as clearly seen from the results of this test, in the SYTO9/PI plot for the LP-treated and EMA-treated (LPE-treated) LTLT non-homogenized milk not inoculated with the bacteria, the SYTO9 intensity was suppressed to a level below $5\times10^2$, and the results were not plotted in the SYTO9(+)·PI(−) region representing presence of live cells.

Moreover, the number of plotted points in the SYTO9(+)·PI(−) region changed depending on the inoculation concentration of *Escherichia coli* (live cells). The numbers of plotted points in this region for each inoculation concentration are shown in Table 7. It is considered that the detection limit of *Escherichia coli* (live cells) in LTLT non-homogenized milk subjected to the LP treatment and the EMA treatment (LPE treatment) is $1.5\times10^4$ cfu/ml under the conditions of this test. Further, LTLT non-homogenized milk inoculated with *Escherichia coli* (injured cells) at a density of $1.5\times10^6$ cfu/ml was subjected to the LPE treatment, and the number of plotted points in the SYTO9(+)·PI(−) region suggesting the presence of live cells was examined. As a result, plotted points hardly existed in the region. Therefore, the LPE treatment enabled clear distinction of live cells and injured cells of *Escherichia coli*.

TABLE 7

Results of detection of live *Escherichia coli*
in LPE-treated LTLT non-homogenized milk

| Number of inoculated bacteria (cfu/ml) | FCM count (actually measured value) |
| --- | --- |
| 0 | 1 |
| $1.5 \times 10^2$ | 20 |
| $1.5 \times 10^3$ | 20 |
| $1.5 \times 10^4$ | 31 |
| $1.5 \times 10^5$ | 349 |
| $1.5 \times 10^6$ | 2095 |

The results of measurement of the numbers of plotted points in the SYTO9(+)·PI(−) region for *Staphylococcus epidermidis* are shown in Table 8. According to the results, the detection limit for *Staphylococcus epidermidis* (live cells) in the UHT homogenized milk was $1.8 \times 10^5$ cfu/ml. It is considered that the causes for the higher detection limit compared with that for *Escherichia coli* are similar to those mentioned in Example 2.

TABLE 8

Results of detection of live *Staphylococcus epidermidis*
in LPE-treated LTLT non-homogenized milk

| Number of inoculated bacteria (cfu/ml) | FCM count (actually measured value) |
| --- | --- |
| 0 | 1 |
| $1.8 \times 10^2$ | 2 |
| $1.8 \times 10^3$ | 2 |
| $1.8 \times 10^4$ | 1 |
| $1.8 \times 10^5$ | 13 |
| $1.8 \times 10^6$ | 85 |
| $1.8 \times 10^7$ | 530 |

Example 4

Examination of effect of various topoisomerase poisons and DNA gyrase poisons

Examination was performed about detection by flow cytometer of *Escherichia coli* (live cells) and *Staphylococcus epidermidis* (live cells) suspended in commercial cow's milk by using compounds belonging to other topoisomerase poisons (amsacrine, ellipticine, camptothecin) and a compound belonging to DNA gyrase poisons (ciprofloxacin), of which activity is similar to that of ethidium monoazide used in Examples 1 and 2.

(1) Preparation of Samples

To 1 ml of $7.5 \times 10^7$ cfu/ml *Escherichia coli* suspension (live cells) prepared in the same manner as that in Control Example 1, 9 ml of the UHT homogenized milk was added to dilute the suspension 10 times and thereby prepare UHT homogenized milk inoculated with $7.5 \times 10^6$ cfu/ml *Escherichia coli* (live cells).

Further, to 1 ml of $2.0 \times 10^8$ cfu/ml *Staphylococcus epidermidis* suspension (live cells) prepared in the same manner as that in Control Example 1, 9 ml of the UHT homogenized milk was added to dilute the suspension 10 times and thereby prepare UHT homogenized milk inoculated with $2.0 \times 10^7$ cfu/ml *Staphylococcus epidermidis* (live cells). Separately, UHT homogenized milk not inoculated with the bacteria was also prepared.

Each of the UHT homogenized milk inoculated with *Escherichia coli* (live cells), UHT homogenized milk inoculated with *Staphylococcus epidermidis* (live cells), and UHT homogenized milk not inoculated with the bacteria in a volume of 1 ml was put into a 2-ml volume microtube, and subjected to a lipase treatment and proteinase K treatment (LP treatment) in the same manner as that in Control Example 1. 880 μl of physiological saline was added to the sample, and the sample was subjected to refrigerated centrifugation at 4° C. and 14,000×g for 10 minutes. The lipid layer of the upper layer was removed with a swab, and the aqueous layer of the middle layer was also removed. Then, 1 ml of physiological saline was added to the cells of the lower layer (precipitates) to prepare each LP-treated suspension.

Each LP-treated suspension was subjected to a treatment with each of a) amsacrine, b) ellipticine, c) camptothecin, and d) ciprofloxacin solutions, and the SYTO9/PI fluorescence staining reagent was added to the suspension to prepare each sample for FCM measurement. Specific procedures are as shown in a) to d) described below.

a) Amsacrine Treatment

To each LP-treated suspension, 10 μl of a solution dissolving amsacrine (Sigma, catalog number: A9809) in dimethyl sulfoxide (DMSO) at a concentration of 1 mg/ml was added, and the mixture was left at 37° C. for 10 minutes. Then, sterilized water was added to the mixture to make the total volume 2 ml, and the mixture was subjected to refrigerated centrifugation at 4° C. and 14,000×g for 10 minutes. After the aqueous layer of the upper layer was removed, 300 μl of physiological saline was added to the pellet of the lower layer, then 0.9 μl of the SYTO9/PI fluorescence staining reagent was added to the mixture, and the reaction was allowed at room temperature for 15 minutes under light shielding to prepare a sample.

b) Ellipticine Treatment

To each LP-treated suspension, 5 μl of a solution dissolving ellipticine (Sigma, catalog number: E3380) in dimethyl sulfoxide (DMSO) at a concentration of 0.1 mg/ml was added, and the mixture was left at 37° C. for 30 minutes. Then, sterilized water was added to the mixture to make the total volume 2 ml, and the mixture was subjected to refrigerated centrifugation at 4° C. and 14,000×g for 10 minutes. After the aqueous layer of the upper layer was removed, 300 μl of physiological saline was added to the pellet of the lower layer, then 0.9 μl of the SYTO9/PI fluorescence staining reagent was added to the mixture, and the reaction was allowed at room temperature for 15 minutes under light shielding to prepare a sample.

c) Camptothecin Treatment

To each LP-treated suspension, 10 μl of a solution dissolving camptothecin (Sigma, catalog number: C9911) in dimethyl sulfoxide (DMSO) at a concentration of 1 mg/ml was added, and the mixture was left at 37° C. for 30 minutes. Then, sterilized water was added to the mixture to make the total volume 2 ml, and the mixture was subjected to refrigerated centrifugation at 4° C. and 14,000×g for 10 minutes. After the aqueous layer of the upper layer was removed, 300 μl of physiological saline was added to the pellet of the lower layer, then 0.9 μl of the SYTO9/PI fluorescence staining reagent was added to the mixture, and the reaction was allowed at room temperature for 15 minutes under light shielding to prepare a sample.

d) Ciprofloxacin Treatment

To each LP-treated suspension, 8 μl of a solution dissolving ciprofloxacin (Fluka, catalog number: 17850) in dimethyl sulfoxide (DMSO) at a concentration of 0.5 mg/ml was added, and the mixture was left at 37° C. for 30 minutes. Then, sterilized water was added to the mixture to make the total volume 2 ml, and the mixture was subjected to refrigerated centrifugation at 4° C. and 14,000×g for 10 minutes. After the aqueous layer of the upper layer was removed, 300 μl of physiological saline was added to the pellet of the lower layer, then 0.9 μl of the SYTO9/PI fluorescence staining reagent was added to the mixture, and the reaction was allowed at room temperature for 15 minutes under light shielding to prepare a sample.

(2) Test Method

FCM measurement was performed for each of the samples prepared above (measurement time: 5 minutes) in the same manner as that in Control Example 1.

(3) Test Results

Figure 8A:
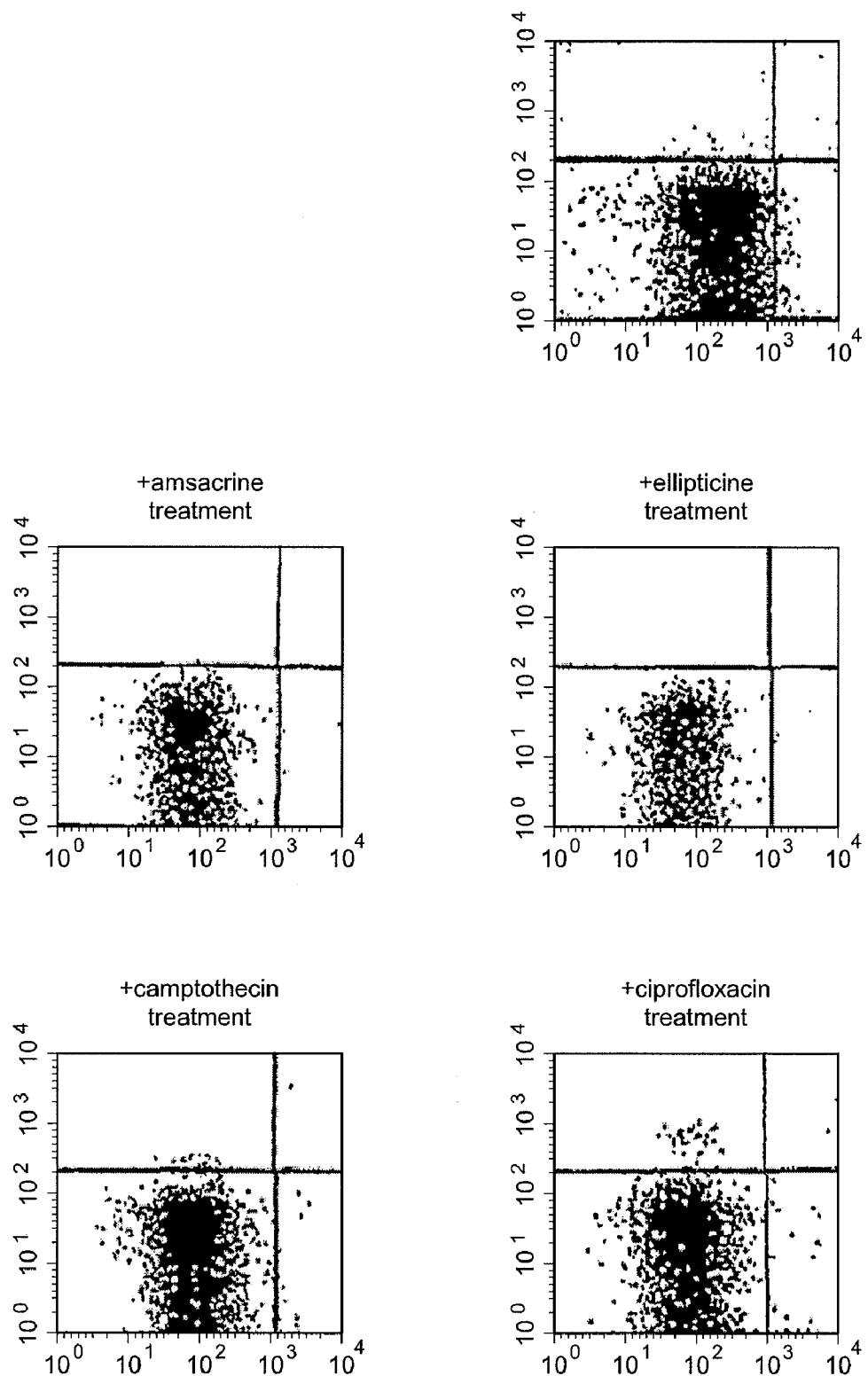
FIG. 8A shows results without bacterial inoculation.
Figure 8B:
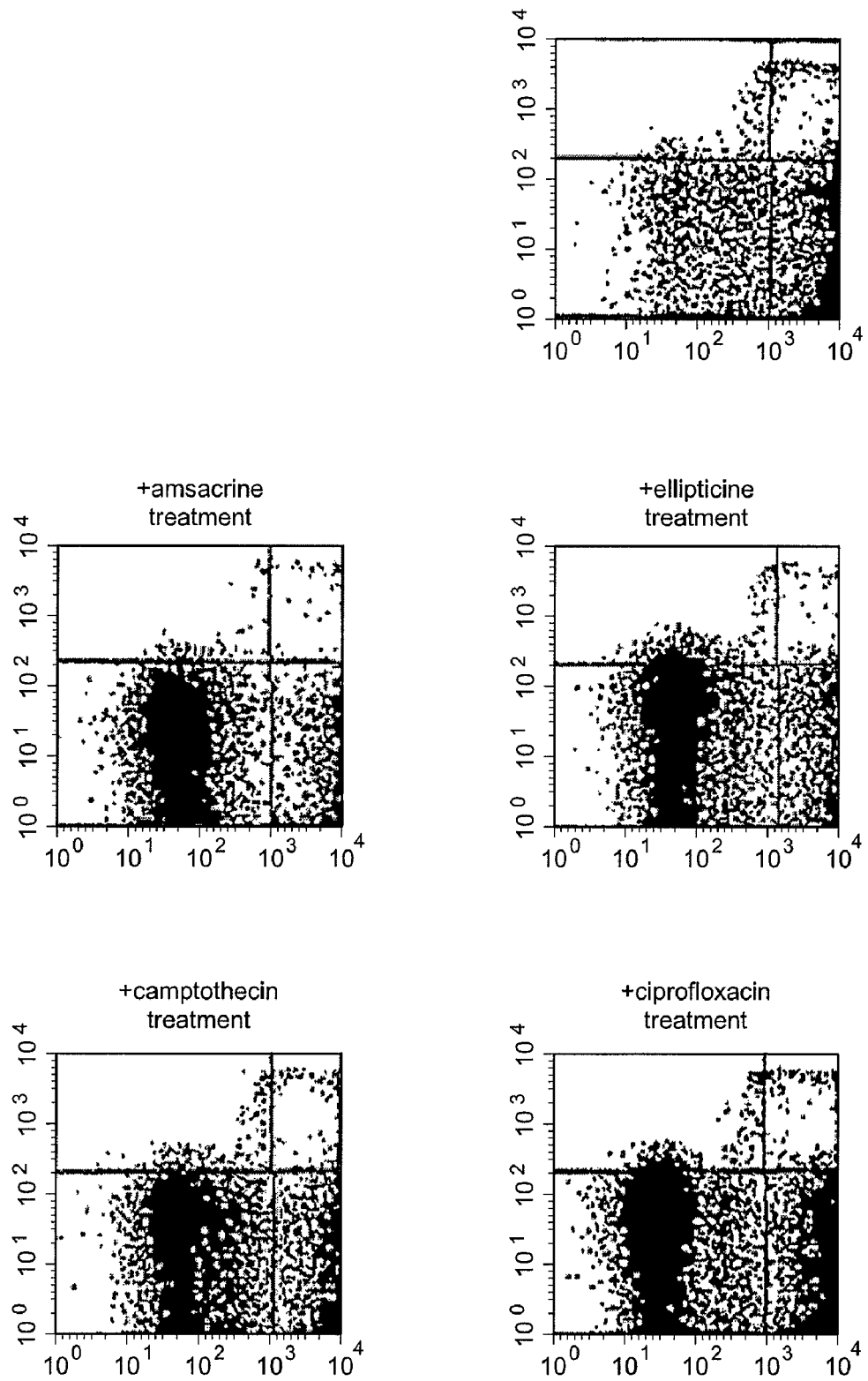
FIG. 8B shows UHT homogenized milk inoculated with Escherichia coli (live bacteria) after LP-treatment.
Figure 8C:
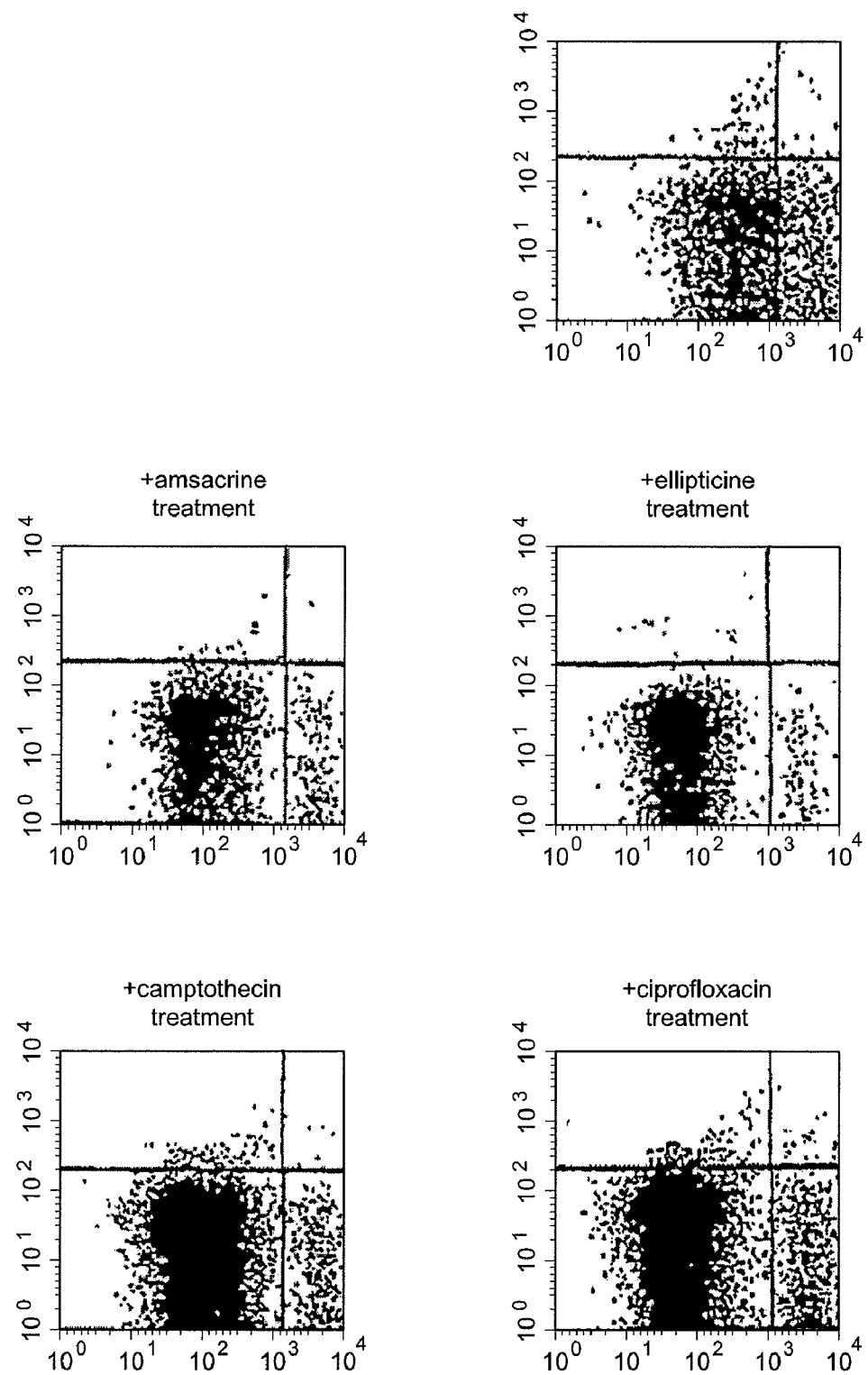
FIG. 8C shows UHT homogenized milk inoculated with *Staphylococcus epidermidis* (live bacteria) after LP-treatment.

The results of this test are shown in FIG. 8.

For the samples subjected to the LP treatment alone, the plotted area of *Escherichia coli* (live cells) and that of the contaminants (somatic cells, injured cells, incomplete degradation products of micellar casein produced by the LP treatment) originated in the UHT homogenized milk were adjacent to each other, and partially overlapped (the SYTO9 intensity of the LP-treated UHT homogenized milk not inoculated with bacteria due to contaminants may significantly exceed $10^3$ depending on type, manufacturer etc. of the cow's milk, and in such a case, the plotted areas of live cells and contaminants significantly overlap each other), and thus *Escherichia coli* (live cells) could not clearly distinguished. However, when the treatment with a solution of a) amsacrine, b) ellipticine, c) camptothecin or d) ciprofloxacin was performed after the LP treatment, the plotted areas of the *Escherichia coli* (live cells) and the contaminants were clearly separated, and as a result, detection of *Escherichia coli* (live cells) became easy. Moreover, similar effect was also observed for *Staphylococcus epidermidis*.

It was highly possible that amsacrine and camptothecin did not penetrate cell walls of *Escherichia coli* or *Staphylococcus epidermidis* (live cells) at the concentrations used in Example 3 within the reaction times mentioned above (10 minutes and 30 minutes, respectively), whereas they penetrated cell membranes of somatic cells which were made dead cells by the flash pasteurization, and cell wall of injured cells. It is considered as follows. Two kinds of the aforementioned agents having penetrated into the somatic cells and injured cells disorderly bind to chromosomal DNAs by covalent attachment to inhibit religation of DNAs by topoisomerase II or topoisomerase I in somatic cells, or topoisomerase IV, topoisomerase I, or topoisomerase III in injured cells, or DNA gyrase, and thereby chromosomal DNAs were fragmented, resulting in decrease of the fluorescence intensity of SYTO9. On the other hand, they do not affect chromosomal DNAs of live cells, and thus the fluorescence intensity of SYTO9 does not decrease in live cells. Therefore, the plotted areas of them were clearly separated.

It was highly possible that ellipticine and ciprofloxacin also did not penetrate cell walls of live cells at the concentrations used in Example 3 within the reaction time mentioned above (30 minutes), whereas they penetrated cell membranes of somatic cells and cell wall of injured cells, alike the aforementioned case. Although it is considered that ellipticine utilizes actions of topoisomerase II in somatic cells and DNA gyrase in injured cells, or topoisomerase IV, it does not inhibit religation of DNAs by these enzymes, but it promotes cleavage of DNA strands by these enzymes to fragment chromosomal DNAs. In contrast, it is considered to be highly possible that ciprofloxacin inhibits religation of DNA strands by DNA gyrase in injured cells, and also inhibits religation of DNA strands by topoisomerase II in somatic cells.

Example 5

Distinction of live cells, injured cells and dead cells based on electrophoretic patterns of chromosomal DNAs obtained after EMA treatment for four kinds of gram-negative bacteria (*Escherichia coli* DH5α, *Klebsiella*, *Citrobacter* and *Salmonella* bacteria) and gram-positive bacterium (*Staphylococcus epidermidis*) used as test materials (1) Preparation of Samples 1-1) Preparation of Suspensions of Four Kinds of Gram-Negative Bacteria (Live Cells, Injured Cells and Dead Cells)

*Escherichia coli* DH5α, *Klebsiella oxytoca* JCM 1665 (henceforth also referred to as "*Klebsiella*"), *Citrobacter koseri* JCM 1658 (henceforth also referred to as "*Citrobacter*"), and *Salmonella enteritidis* IID 604 (henceforth also referred to as "*Salmonella*") were cultured at 37° C. in BHI broth, and 40 ml of each medium in which the cells were at a later stage of logarithmic growth phase was subjected to refrigerated centrifugation at 4° C. and 8,000×g for 15 minutes. The supernatant was removed, then 40 ml of physiological saline was added to the residue, the mixture was stirred and subjected to refrigerated centrifugation of the same conditions. The supernatant was removed, and 10 ml of physiological saline was added to the residue to prepare a live cell suspension. The live cell counts of these live cell suspensions were *Escherichia coli*: $3.2 \times 10^8$ cfu/ml, *Klebsiella*: $4.8 \times 10^8$ cfu/ml, *Citrobacter*: $6.7 \times 10^7$ cfu/ml, and *Salmonella*: $1.9 \times 10^8$ cfu/ml. Further, 1 ml of each live cell suspension was put into a 1.5 ml microtube, and the microtube was immersed in boiling water for 50 seconds, and then rapidly cooled by immersion in ice water to prepare an injured cell suspension. Furthermore, as for *Escherichia coli*, a dead cell suspension was separately prepared from 1 ml of the live cell suspension by immersion in boiling water for 12 minutes and rapid cooling in ice water. It was confirmed that both the injured cell and dead cell suspensions did not form colonies on L agar medium.

1-2) Preparation of Suspensions Gram-Positive Bacterium (Live Cells, Injured Cells and Dead Cells)

*Staphylococcus epidermidis* (*Staphylococcus epidermidis* KD strain) was cultured at 37° C. in BHI broth, and 40 ml of the medium in which the cells were at the logarithmic growth phase was subjected to refrigerated centrifugation at 4° C. and 8,000×g for 15 minutes. The supernatant was removed, then 40 ml of physiological saline was added to the residue, and the mixture was sufficiently stirred and then subjected to refrigerated centrifugation of the same conditions. The supernatant was removed, and 10 ml of physiological saline was added to the residue to prepare a live cell suspension. The live cell count of this live cell suspension was $1.9 \times 10^8$ cfu/ml. Further, 1 ml of the live cell suspension was put into a 1.5 ml microtube, and the microtube was immersed in boiling water for 50 seconds, and then rapidly cooled by immersion in ice water to prepare an injured cell suspension. Furthermore, a dead cell suspension was separately prepared from 1 ml of the live cell suspension by immersion in boiling water for 12 minutes and rapid cooling in ice water. It was confirmed that both the injured cell and dead cell suspensions did not form colonies on L agar medium.

In order to prepare a plot of immersion time in boiling water/liquid temperature in advance, 1 ml of physiological saline was put into a 1.5 ml microtube at room temperature and completely sealed with a lid, a small hole was made on the lid, and a thermocouple type temperature sensor (TX10, Yokogawa M & C) was put into the hole. Then, the microtube was substantially completely immersed in boiling water, and the temperature of the liquid was measured over time.

(2) Test Method
2-1) Ethidium Monoazide Treatment and Visible Light Irradiation Steps In a volume of 1 ml each suspension of the gram-negative bacteria (live cells, injured cells and dead cells) and gram-positive bacterium (live cells, injured cells and dead cells) was subjected to an EMA treatment in the same manner as that in Example 3. After addition of the EMA solution to the suspensions, the suspensions of the gram-negative bacteria were left at 4° C. for 30 minutes under light shielding, and those of the gram-positive bacterium were left at 4° C. for 5 minutes under light shielding, until they were subjected to visible light irradiation. Separately, 10 µl of sterilized water was added to 1 ml of each suspension of the gram-negative bacteria (live cells, injured cells and dead cells) and gram-positive bacterium (live cells, injured cells and dead cells), instead of the EMA solution, and then subjected to the same procedure used for the aforementioned EMA treatment (EMA-untreated).

2-2) DNA Extraction Step

Each of the microtubes containing live cells, injured cells and dead cells of the gram-negative bacteria and gram-positive bacterium (EMA-untreated and treated) was subjected to refrigerated centrifugation at 4° C. and 15,000×g for 10 minutes, and the supernatant was removed. To each microtube, 1 ml of physiological saline was added, the mixture was sufficiently stirred, and then the total volume of the mixture was transferred to a 2 ml microtube and subjected to refrigerated centrifugation at 4° C. and 15,000×g for 10 minutes. The supernatant was removed to obtain a cell pellet.

As for the gram-positive bacterium, DNAs were extracted by the following method. To each cell pellet, 0.5 ml of 5 mM EDTA was added, and 20 µl of an achromopeptidase solution prepared beforehand at 5 mg/ml with 10 mM NaCl aqueous solution (Wako Pure Chemical Industries, catalog number: 014-09661) was added, and the mixture was left at 50° C. for 30 minutes. Then, to the mixture, 0.5 ml of 10 mM Tris-HCl (pH 8.0) was added, 20 µl of 1250 U/ml proteinase K (Sigma, catalog number: E.C. 3.4.21.64) was added, 400 µl of an SDS solution prepared beforehand at 10% (w/v) with sterilized water was added, and the reaction was allowed overnight at 50° C.

Each treated suspension was put into two 2 ml volume microtubes in a half volume each, 0.5 ml of saturated phenol was added to the suspension, and the mixture was gently stirred for 15 minutes. Then, 0.5 ml of chloroform was added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 70 µl of 3 M sodium acetate (pH 5.2) and 1.21 ml of 99.5% cold ethanol were added to the mixture, and the mixture was gently stirred. The mixture was subjected to refrigerated centrifugation at 4° C. and 15,000×g for 10 minutes, the supernatant was removed, and then the residue was washed with 0.4 ml of 70% cold ethanol (the aforementioned procedure is also referred to as the "phenol/chloroform extraction"). 0.5 ml of TE buffer (10 mM Tris-HCl, 1 mM EDTA.2Na) was added to the pellet, and the mixture was left overnight at 4° C. to dissolve DNAs.

5 µl of an RNase (Sigma, catalog number: E.C. 3.1.27.5) solution prepared beforehand at 10 mg/ml with sterilized water was added to the aforementioned DNA solution, and the mixture was incubated at 37° C. for 1 hour. 0.25 ml of phenol/chloroform (1/1) was added to the mixture, the mixture was gently stirred for 10 minutes, 0.25 ml of chloroform was further added to the mixture, and the mixture was gently stirred for 5 minutes. The mixture was subjected to refrigerated centrifugation at 4° C. and 6,000×g for 10 minutes, the aqueous layer of the upper layer was transferred to a new 2 ml volume microtube, 50 µl of 3 M sodium acetate aqueous solution and 1 ml of 99.5% cold ethanol were added to the mixture, and the mixture was gently stirred. The mixture was subjected to refrigerated centrifugation at 4° C. and 15,000×g for 10 minutes, the supernatant was removed, then the residue was washed with 0.4 ml of 70% cold ethanol, and the pellet was dried (the aforementioned procedure is also referred to as the "RNase treatment"). 125 µl of TE buffer was added to the dried pellet, and the mixture was left overnight at 4° C. to dissolve DNAs. Concentration of the purified DNA solution was measured based on absorbance at 260 nm (UV), $OD_{260}$ (50 µg of DNA/ml was considered OD=1, cell length: 1 cm), and purity of the purified DNA was estimated on the basis of $OD_{260}/OD_{280}$.

As for the gram-negative bacteria, DNA was extracted by the following method. To the aforementioned cell pellet, 0.5 ml of 10 mM Tris-HCl (pH 8.0) was added, 10 µl of 1250 U/ml proteinase K (Sigma, catalog number: E.C. 3.4.21.64) was added, and 200 µl of an SDS solution prepared beforehand at 10% (w/v) with sterilized water was added, and the reaction was allowed overnight at 50° C. Thereafter, DNA extraction was performed in the same manner as that of the DNA extraction step for the gram-positive bacterium.

2-3) Agarose Gel Electrophoresis of Extracted DNA

From Seakem GTG agarose (FMC, catalog number: 50070) and TAE buffer (4.84 g/L of Tris, 1.142 ml/L of acetic acid, 0.149 g/L of EDTA.2Na), 0.8% agarose gel was prepared, and λ-EcoT14I digest (Takara Shuzo, Code: 3401) and 100 bp DNA Ladder (Takara Shuzo, Code: 3407A) were used as markers. For each of the gram-negative bacteria and gram-positive bacterium, the EMA-untreated live cell suspension, EMA-treated live cell suspension, EMA-untreated injured cell suspension and EMA-treated injured cell suspension were applied into wells in this order in an amount of about 1 µg, and subjected to electrophoresis at 100 V. When bromphenol blue (BPB) migrated about 90% in the gel, the electrophoresis was terminated. Separately, for *Escherichia coli* and *Staphylococcus epidermidis*, the EMA-untreated dead cell suspension and EMA-treated dead cell suspension were also subjected to similar electrophoresis.

The gel on which the electrophoresis was performed was immersed in 1 µg/ml ethidium bromide aqueous solution for 20 minutes and washed twice with Milli-Q water, and then degree of chromosomal DNA cleavage was observed by using a UV transilluminator (254 nm).

(3) Test Results

Figure 9:
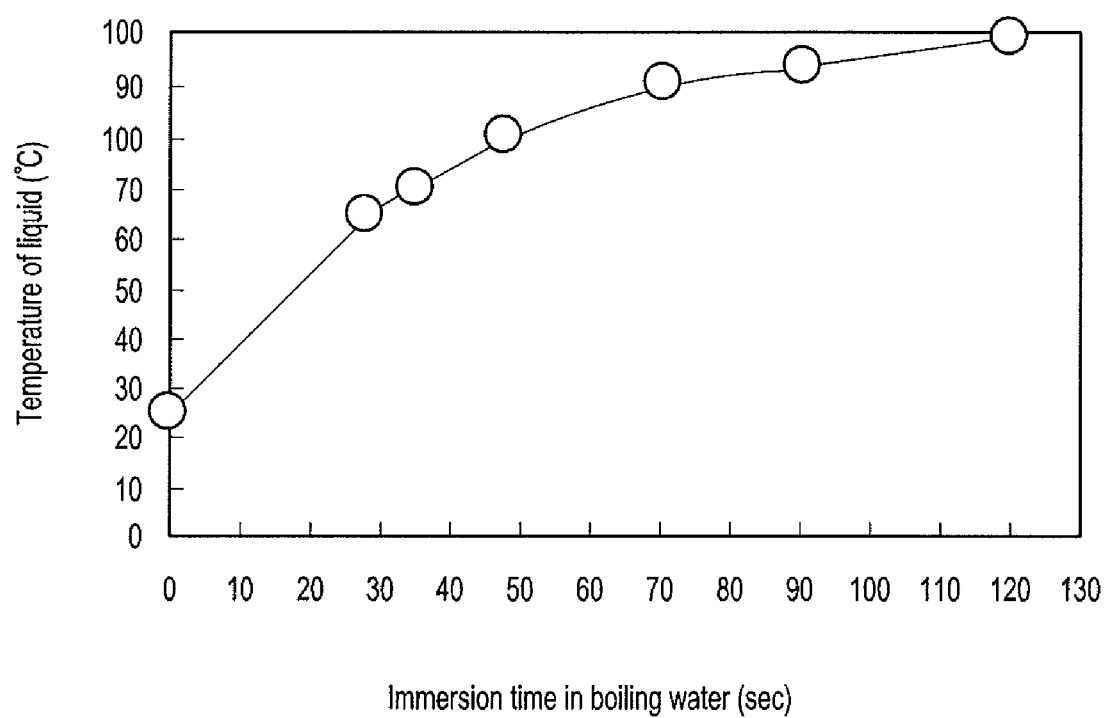
[FIG. 9] Graph showing the relationship of immersion time in boiling water of a microtube containing physiological saline and temperature of liquid in the microtube.

The relationship between the immersion time in boiling water and the liquid temperature is shown in FIG. 9. It was confirmed that at least the heat treatment by immersion in boiling water for 50 seconds corresponded to a pasteurization treatment slightly stronger than the high temperature short time pasteurization (HTST pasteurization, 72 to 75° C., 15 to 16 seconds). Therefore, it was confirmed that the aforementioned heat treatment was equivalent to a heat treatment of the same degree as that of sterilization for suppressing denaturation of foodstuffs, i.e., low temperature long time pasteurization (LTLT pasteurization) and ultrahigh temperature pasteurization (UHT pasteurization). Therefore, the injured cells prepared by the method described in (1) Preparation of samples mentioned above are biochemically and enzymologically equivalent to dead cells in foodstuffs killed for the purpose of suppressing denaturation of ingredients of the foodstuffs, and physical injuries are also equivalent. For the dead cells prepared by the method described in (1) Preparation of samples mentioned above, since the liquid temperature was maintained at 100° C. for 10 minutes after the temperature reached 100° C., and the suspension was also heated for 2 minutes before the temperature reached 100° C. according to the relationship shown in FIG. 9, most of the enzymes in the dead cells were inactivated, and injuries of cell walls were also so severe that a part of chromosomal DNAs flew out of the cells.

Figure 10:
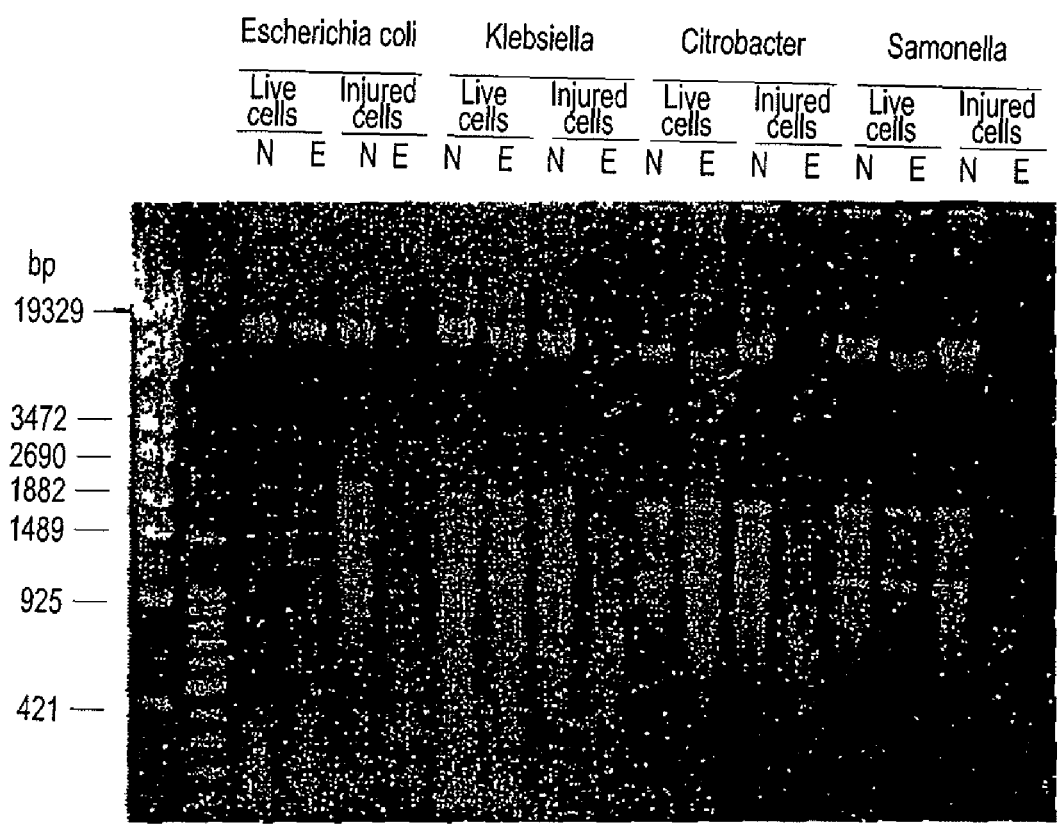
[FIG. 10] Electrophoresis photographs of chromosomal DNAs of *Escherichia coli, Klebsiella, Citrobacter* and *Salmonella* (live bacteria and injured bacteria) extracted and purified before (N) or after (E) the EMA treatment.

Next, the results of distinction of live cells and injured cells of each gram-negative bacterium are shown in FIG. 10, the results of distinction of injured cells and dead cells of *Escherichia coli* in FIG. 11, and the results of distinction of live cells, injured cells and dead cells of the gram-positive bacterium (*Staphylococcus epidermidis*) are shown in FIG. 12. In FIG. 10, the extremely long band (LL band) originated in chromosomal DNA located slightly under the λ-EcoT14I digest marker 19329 bp was noted, and it was defined that presence of this band was indicated as (+), and absence of this band was indicated as (−). The results of the four kinds of the gram-negative bacteria for that band were, in the order of EMA-untreated and EMA-treated samples, (+)·(+) pattern for live cells, and (+)·(−) pattern for injured cells. Further, the patterns of injured cells and dead cells of *Escherichia coli* shown in FIG. 11 were (+)·(−) pattern and (−)·(−) pattern, respectively. Therefore, simultaneous distinction of live cells, injured cells and dead cells was enabled by EMA. FIG. 12 similarly shows that distinction of live cells, injured cells and dead cells is also possible for a gram-positive bacterium such as *Staphylococcus epidermidis*.

EMA acts on, in particular, topoisomerase II in human tumor cells showing high mitotic rate, as a topoisomerase II poison of mammalian cells, and inhibits the religation of DNAs among the actions of the enzyme, DNA cleavage and religation. Therefore, it is expected as anticancer agent that cleaves chromosomal DNAs of cancer cells everywhere to kill the cancer cells. EMA originally shows weak cell membrane permeability, and in applications in the field of bacteriology, it is ranked only as a so-called DNA crosslinking agent, which cannot penetrate cell walls of live bacteria, but can penetrate cell walls of dead bacteria to crosslink chromosomal DNAs of dead bacteria, as described in International Patent Application Unexamined Publication in Japan No. 2003-530118. Also in this example, there was no phenomenon that chromosomal DNAs of live cells were specifically cleaved by the action of EMA allowed for 30 minutes as shown in FIG. 10, and chromosomal DNAs of injured cells were clearly suffered from severe cleavage by the action of EMA allowed for the same duration. Therefore, it was suggested that EMA did not penetrate cell walls of live cells so much, but it penetrated most of cell walls of injured cells. What should be especially mentioned is that, although EMA originally inhibits the action of topoisomerase II of mammalian cells for religation and thereby causes cleavage of chromosomal DNAs everywhere, resulting in death of the mammalian cells, EMA did not affect live cells in this example, and it can be construed that it inhibits the activities of bacterial DNA gyrase and/or topoisomerase IV of which activities remain in the cells, and causes cleavage of chromosomal DNAs of injured cells everywhere.

Example 6

Simultaneous distinction of EMA-treated live cells, injured cells and dead cells of *Escherichia coli* and *Staphylococcus epidermidis* by FCM (1) Preparation of Samples
1-1) Preparation of Suspensions of *Escherichia coli* (Live Cells, Injured Cells and Dead Cells)

According to the method of Example 5, (1) Preparation of samples, 1-1), live cells, injured cells and dead cells of *Escherichia coli* were prepared (live cell count: $4\times10^6$ cfu/ml, injured cell count: $4\times10^6$ cfu/ml, dead cell count: $4\times10^6$ cfu/ml).

1-2) Preparation of Suspensions of *Staphylococcus Epidermidis* (Live Cells, Injured Cells and Dead Cells)

According Example 5, (1) Preparation of samples, 1-2), live cells, injured cells and dead cells of *Staphylococcus epidermidis* were prepared (live cell count: $4\times10^7$ cfu/ml, injured cell count: $4\times10^7$ cfu/ml, dead cell count: $4\times10^7$ cfu/ml).

(2) Test Method
2-1) Ethidium Monoazide Treatment and Visible Light Irradiation Step To each of 1 ml of the aforementioned suspensions of live cells, injured cells and dead cells of *Escherichia coli*, 10 µl of a 1000 µg/ml EMA aqueous solution was added, and the suspension was left at 4° C. for 30 minutes under light shielding. Then, the suspension was placed on ice, and irradiated with visible light of 500 W from a lamp (FLOOD PRF, 100 V, 500 W, Iwasaki Electric Co., Ltd.) disposed at a distance of 20 cm from the suspension for 10 minutes. The live cells, injured cells and dead cells of *Staphylococcus epidermidis* were subjected to the same treatment.

2-2) Nuclear Staining and FCM Measurement

Each of the aforementioned EMA-treated suspensions was subjected to refrigerated centrifugation at 4° C. and 15,000×g for 15 minutes. After the supernatant was removed, 1 ml of physiological saline was added to the residue, and the mixture was sufficiently stirred, and subjected to refrigerated centrifugation of the same conditions. The supernatant was removed, and 1 ml of physiological saline was added to the residue. 3 µl of an SYTO9/PI fluorescence staining reagent (LIVE/DEAD BacLight™ Bacterial Viability kit, Molecular Probes, SYTO9/PI=1/1 mixture) was added to the mixture, and the reaction was allowed at room temperature for 15 minutes under light shielding to prepare each sample suspension. For these samples, measurement was performed by using an FCM measurement apparatus, FACS Calibur (Becton Dickinson). The measurement conditions were the same as those of Control Example 1.

(3) Test Results

Figure 14:
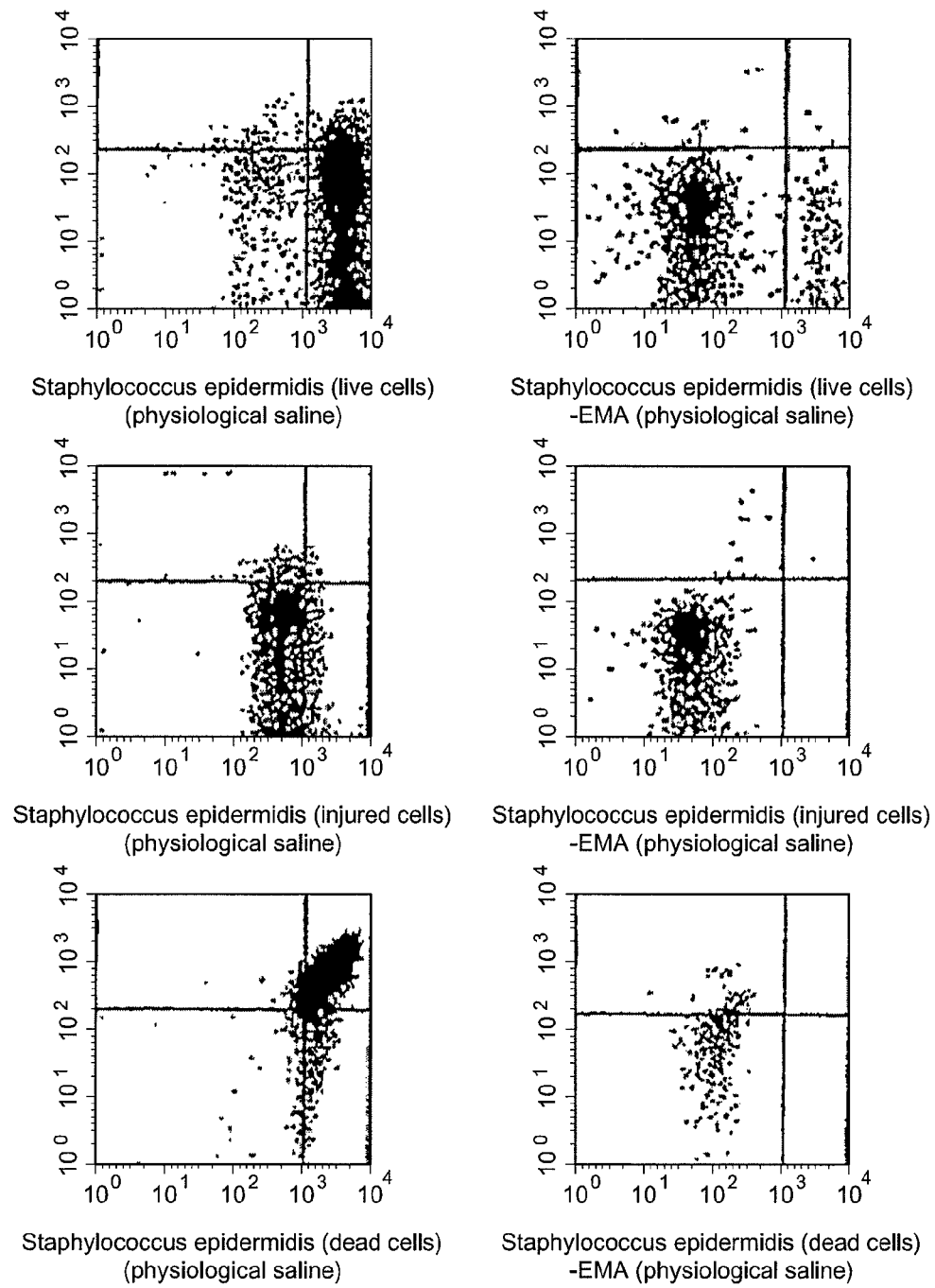
[FIG. 14] Graphs showing the results of FCM measurement for live bacteria, injured bacteria and dead bacteria of *Staphylococcus epidermidis* before and after the EMA treatment.

The results of the test by FCM for the live cells, injured cells and dead cells of *Escherichia coli* before and after the EMA treatment are shown in FIG. 13, and such results for *Staphylococcus epidermidis* are shown in FIG. 14.

The boundary value of the intensity of the staining with SYTO9 is defined to be an intensity of $10^3$, results exceeding that value are represented as SYTO9(+), and results lower than that value are represented as SYTO9(−). The boundary value of the intensity of the staining with PI is defined to be an intensity of $2\times10^2$, results exceeding that value are represented as PI(+), and results lower than that value are represented as PI(−). The live cells of *Escherichia coli* before the EMA treatment mainly distributed in the SYTO9(+)·PI(−) region, the injured cells also mainly distributed in the SYTO9(+)·PI(−) region, and the dead cells mainly distributed in the SYTO9(+)·PI(+) region. That is, for the cells not treated with EMA, the live cells and the injured cells could not be distinguished, but the injured cells and the dead cells could be distinguished even if the cells were not treated with EMA. Furthermore, after the EMA treatment, distribution of the live cells did not change, i.e., they distributed in the SYTO9(+)·PI(−) region, but the intensity of staining with SYTO9 for injured cells markedly decreased to shift the main distribution thereof to the SYTO9(−)·PI(−) region, and thus the live cells and the injured cells could be clearly distinguished. With no treatment, simultaneous distinction of the live cells, injured cells and dead cells was impossible. However, after the EMA treatment, although the main distribution of dead cells shifted from the SYTO9(+)·PI(+) region to the SYTO9(−)·PI(+) region, the regions in which the live cells, injured cells and dead cells mainly distributed did not overlap, and thus simultaneous distinction was possible.

In the case of injured cells, the enzymatic activity in the injured cells remains, and there are also metabolic activities. Therefore, EMA penetrates cell walls of injured cells and crosslink chromosomal DNAs of the injured cells to inhibit the action for religation of the bacterial DNA gyrase in the injured cells. As a result, the state that the chromosomal DNAs are cleaved everywhere is maintained, and the chromosomal DNAs are significantly fragmented. This especially leads to decrease in the number of intercalating SYTO9, and therefore the staining intensity decreases. In the case of the dead cells, metabolic functions are terminated, and genes are not transcribed. However, it is suggested that since the bacterial DNA gyrase and bacterial topoisomerase IV have heat resistance, a part of the activities thereof remain, and thus the aforementioned enzymes function by themselves. Therefore, it is estimated that if the EMA treatment is performed, the intensity of staining with SYTO9 is markedly decreased.

Example 7

Simultaneous distinction of live cells, injured cells and dead cells of *Mycobacterium tuberculosis* (*Mycobacterium tuberculosis* H37RA, henceforth also referred to as "*Mycobacterium tuberculosis*") and *Listeria monocytogenes* (*Listeria monocytogenes* JCM 2873, henceforth also referred to as "*Listeria*") by FCM (1) Preparation of Samples 1-1) Preparation of Suspensions of *Mycobacterium Tuberculosis* (Live Cells, Injured Cells and Dead Cells)

*Mycobacterium tuberculosis* was applied on an agar slant of the Ogawa medium, and cultured at 37° C. for 3 weeks (in an environment of 20% oxygen and 5% carbon dioxide). Then, the cells were inoculated into the Sauton's liquid medium containing 0.05% Tween 80, and cultured at 37° C. for 3 weeks under the aforementioned aerobic condition. The culture medium was serially diluted with physiological saline containing 0.05% Tween 80, and cultured on a Middlebrook 7H10 agar medium plate to confirm that the live cell count was $7.7 \times 10^8$ cfu/ml. The culture medium in a volume of 2 ml was inoculated into 200 ml of newly prepared Sauton's liquid medium containing 0.05% Tween 80, 200 µl of 150 mg/ml rifampicin solution (dissolved in sterilized water) was added to the culture (final concentration: 148.5 µg/ml), 100 µl of 10 mg/ml of isonicotinic acid hydrazide (dissolved in sterilized water) was further added to the medium (final concentration: 5 µg/ml), and the cells were cultured at 37° C. for 3 months under the aforementioned aerobic condition. After the culture for 1 month, the live cell count of *Mycobacterium tuberculosis* was measured on the 7H10 medium, and it was confirmed that the cells did not form colonies.

The culture medium after the culture of 3 months in a volume of 200 ml was subjected to refrigerated centrifugation at 4° C. and 8,000×g for 10 minutes, the supernatant was completely removed, then 200 ml of physiological saline containing 0.05% Tween 80 was added to the residue, the mixture was stirred and subjected to refrigerated centrifugation under the same conditions as mentioned above, and the supernatant was completely removed. The washing operation was further performed once, and it was confirmed that the supernatant did not show brown color originated from rifampicin. To the pellet obtained by the refrigerated centrifugation, 20 ml of physiological saline containing 0.05% Tween 80 was added to prepare a *Mycobacterium tuberculosis* injured cell suspension.

The bacterial cell count in the aforementioned *Mycobacterium tuberculosis* injured cell suspension was measured by the following method. That is, 1 ml of the aforementioned culture medium (live cells) of $7.7 \times 10^8$ cfu/ml of *Mycobacterium tuberculosis* was extracted, and subjected to refrigerated centrifugation at 4° C. and 15,000 rpm for 10 minutes. After the supernatant was removed, 1 ml of physiological saline containing 0.05% Tween 80 was added to the residue, the mixture was stirred and subjected to refrigerated centrifugation under the same condition as mentioned above, and the supernatant was completely removed. To the pellet, 1 ml of physiological saline containing 0.05% Tween 80 was added (*Mycobacterium tuberculosis* live cell suspension, $5.2 \times 10^8$ cfu/ml). The suspension was further diluted 10, 100, 1000 and 10000 times with physiological saline containing 0.05% Tween 80 to prepare diluted suspensions, and absorbance for visible light of 600 nm, $OD_{600\,nm}$, of each suspension was measured. The live cell densities of *Mycobacterium tuberculosis* and the OD values were plotted to prepare a calibration curve, and concentration of injured cells was calculated on the basis of the OD value of the aforementioned *Mycobacterium tuberculosis* injured cell suspension (injured cell count in the *Mycobacterium tuberculosis* injured cell suspension: $6 \times 10^7$ cfu/ml).

A newly prepared live cell suspension of *Mycobacterium tuberculosis* was diluted with physiological saline containing 0.05% Tween 80 to have the same OD value as that of the injured cell suspension.

Further, a *Mycobacterium tuberculosis* live cell suspension of the same density as that of the injured cells was immersed in boiling water for 12 minutes to prepare a *Mycobacterium tuberculosis* dead cell suspension. Since it is impossible to make *Mycobacterium tuberculosis* cells dead cells, not injured cells, or it is uncertain to be able to make *Mycobacterium tuberculosis* cells dead cells, not injured cells, by long term administration of an antituberculous agent in view of the action mechanism of antituberculous agent, dead cells was prepared by the heat treatment.

1-2) Preparation of Suspensions of *Listeria* (Live Cells, Injured Cells and Dead Cells)

*Listeria* was inoculated into L broth and cultured at 30° C. for 48 hours ($3 \times 10^8$ cfu/ml). The culture medium in a volume of 3 ml was inoculated into 300 ml of L broth, 1.5 ml of 100 mg/ml ampicillin solution (dissolved in sterilized water) and 600 µl of 100 mg/ml gentamycin solution (dissolved in sterilized water) were added to the culture medium (final concentrations: 500 µg/ml and 200 µg/ml, respectively), and the cells were cultured at 30° C. for 3 weeks. After the culture, it was confirmed that the cells did not form colonies on L agar medium. The culture medium in a volume of about 200 ml was subjected to refrigerated centrifugation at 4° C. and 8000×g for 15 minutes, and the supernatant was completely removed. To the pellet, 300 ml of physiological saline was added, the mixture was stirred and then subjected to refrigerated centrifugation under the same condition, the supernatant was completely removed, and 3 ml of physiological saline was added to the pellet to prepare a *Listeria* injured cell suspension. By substantially the same procedure as that used for the measurement of injured cell count of *Mycobacterium*

*tuberculosis*, the injured cell count of the *Listeria* injured cell suspension was measured (2×10⁸ cfu/ml).

Separately, a *Listeria* live cell suspension was prepared according to the method of Example 6, (1) Preparation of samples, 1-1), and diluted with physiological saline to such a density that the OD value of the suspension should be the same as the OD value of the *Listeria* injured cell suspension.

Further, a *Listeria* dead cell suspension was prepared by immersing a *Listeria* live cell suspension of the same density as that of the injured cell suspension in boiling water for 12 minutes.

(2) Test Method
2-1) Ethidium Monoazide Treatment and Visible Light Irradiation Steps To each of the aforementioned suspensions of live cells, injured cells and dead cells of *Mycobacterium tuberculosis*, and suspensions of live cells, injured cells and dead cells of *Listeria* in a volume of 1 ml, a 1000 µg/ml EMA aqueous solution was added in a volume of 30 µl for *Mycobacterium tuberculosis* (final concentration: about 30 µg/ml), or 10 µl for *Listeria* (final concentration: about 10 µg/ml), and each suspension was left at 4° C. for 2.5 hours for *Mycobacterium tuberculosis*, or at 4° C. for 5 minutes for *Listeria* under light shielding. Then, the suspension was placed on ice, and irradiated with visible light of 500 W from a lamp (FLOOD PRF, 100 V, 500 W, Iwasaki Electric Co., Ltd.) disposed at a distance of 20 cm from the suspension for 5 minutes.

2-2) Nuclear Staining and FCM Measurement

Each of the aforementioned EMA-treated suspensions was subjected to refrigerated centrifugation at 4° C. and 15,000×g for 15 minutes. After the supernatant was removed, 1 ml of physiological saline containing 0.05% Tween 80 was added to the residue for *Mycobacterium tuberculosis*, or 1 ml of physiological saline for *Listeria*, and the mixture was sufficiently stirred, and subjected to refrigerated centrifugation of the same conditions. The supernatant was removed, and 1 ml of the Sauton's liquid medium containing 0.05% Tween 80 was added to the residue for *Mycobacterium tuberculosis*, or 1 ml of physiological saline for *Listeria*. For *Mycobacterium tuberculosis*, the cells were cultured at 37° C. for 24 hours, then the culture was subjected to refrigerated centrifugation at 4° C. and 15,000×g for 15 minutes, the supernatant was removed, and then 1 ml of physiological saline containing 0.05% Tween 80 was added to the residue.

3 µl of an SYTO9/PI fluorescence staining reagent (LIVE/DEAD BacLight™ Bacterial Viability kit, Molecular Probes, SYTO9/PI=1/1 mixture) was added to each treated mixture, and the reaction was allowed at room temperature for 15 minutes under light shielding to prepare each sample suspension. For these samples, measurement was performed by using an FCM measurement apparatus, FACSCalibur (Becton Dickinson). The measurement conditions were the same as those of Control Example 1.

(3) Test Results

Figure 16:
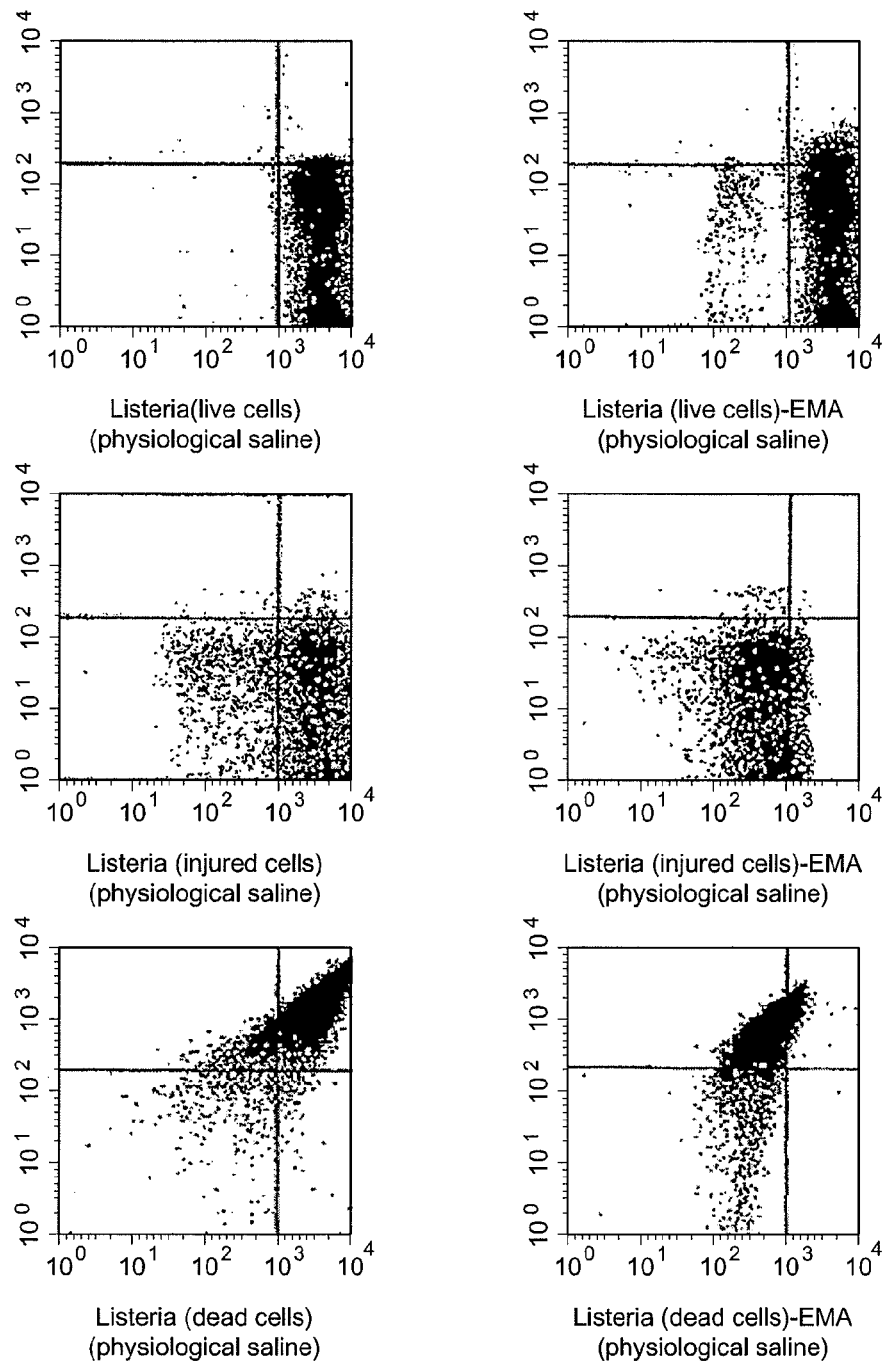
[FIG. 16] Graphs showing the results of FCM measurement for live bacteria of *Listeria* and injured bacteria and dead bacteria of the same treated with ampicillin and gentamycin before and after the EMA treatment.

The results of the test by FCM for the live cells, injured cells treated with isonicotinic acid hydrazide and rifampicin, and dead cells of *Mycobacterium tuberculosis* before and after the EMA treatment are shown in FIG. 15, and the results for the live cells, injured cells treated with ampicillin and gentamycin, and dead cells of *Listeria* before and after the EMA treatment are shown in FIG. 16.

Like Example 6, (3) Test results, the boundary value of the intensity of the staining with SYTO9 is defined to be an intensity of $10^3$, results exceeding that value are represented as SYTO9(+), and results lower than that value are represented as SYTO9(−). The boundary value of the intensity of the staining with PI is defined to be an intensity of $2×10^2$, results exceeding that value are represented as PI(+), and results lower than that value are represented as PI(−). From the results shown in FIG. 15, it is clear that the EMA treatment enables distinction of live cells of *Mycobacterium tuberculosis* and injured cells of *Mycobacterium tuberculosis* treated with isonicotinic acid hydrazide and rifampicin. As for dead cells, distinction from the live cells and the injured cells has already been realized by SYTO9/PI before the addition of EMA. In addition, although the region in which the dead cells mainly distributed shifted from the SYTO9(+)·PI(+) region to the SYTO9(+)·PI(+) region due to the EMA treatment, the region did not overlap with the regions in which the live cells and injured cells treated with EMA mainly distributed. Therefore, simultaneous distinction of live cells, injured cells and dead cells becomes possible. The SYTO9 intensity of the injured cells of *Mycobacterium tuberculosis* was markedly shifted to the left direction by the EMA treatment, and the region was shifted from SYTO9(+)·PI(−) to SYTO9(−)·PI(−) by the EMA treatment. Rifampicin binds to (3-subunit of bacterial DNA-dependent RNA polymerase to inhibit the RNA polymerase to bind a promoter on DNA. As a result, initiation of transcription is prevented. Since it does not act on the RNA polymerase already bound to a promoter, already initiated transcription reaction is not inhibited. Therefore, even if the cells become injured cells which have lost colony formation ability by the addition of rifampicin, activities of various enzymes produced before the addition of rifampicin in the live cells of *Mycobacterium tuberculosis* such as bacterial DNA gyrase and bacterial topoisomerase IV remain, and the cell walls are also maintained in view of the action mechanism of rifampicin. Although isonicotinic acid hydrazide inhibits the mycolic acid synthesis in cell walls, it does not significantly affect the cell walls already formed, either, and thus it does not result in destruction of the cells during cell division. By adding EMA in such a state, religation by bacterial DNA gyrase and/or bacterial topoisomerase IV is inhibited, cleavage phenomena will occur everywhere in chromosomal DNAs as a result, and thus DNAs are fragmented.

It is considered that, therefore, the intercalation efficiency of SYTO9 decreases, and the staining intensity of the injured cells is significantly shifted to the left direction. In the case of dead cells, the intensity of staining with SYTO9 clearly decreased according to the same action mechanism as that of the dead cells mentioned in Example 6. In addition, the live cells, injured cells and dead cells of *Listeria* also showed the same phenomenon as that shown by *Mycobacterium tuberculosis*.

Control Example 4

Preparation and Distinction of Live Cells, Injured Cells and Dead Cells by Conventional Methods
(1) Preparation of Samples and Test Methods
1-1) Application in Food Sanitation Inspection Live cell suspensions in physiology saline of *Escherichia coli* ($2.6×10^3$ to $2.6×10^8$ cfu/ml) and *Staphylococcus epidermidis* ($6.7×10^2$ to $6.7×10^7$ cfu/ml) (A) were prepared, and they were immersed in boiling water for 50 seconds and rapidly cooled (B), or immersed in boiling water for 12 minutes and rapidly cooled (C). In these suspensions of (A), (B) and (C), live cells, injured cells and dead cells were classified by the ATP method and the esterase activity measurement method at the same bacterial densities. Further, it was examined that the various states of bacteria determined to be live cells, injured cells or dead cells by the method of the present invention in Examples 5 and 6 belonged to which classification among those determined by the ATP method (KIKKOMAN ATP measurement reagent kit, Lucifer 250 Plus, and KIKKOMAN ATP eliminating reagent kit, Lucifer ATP Eliminating Reagent, KIKKOMAN CORP.) and the esterase method (Applied and Environmental Microbiology, 2002, 68:5209-5216).

1-2) Application in Clinical Test

Mycobacterium tuberculosis live cell suspensions in physiological saline containing 0.05% Tween (D1, $5.3 \times 10^3$ to $5.3 \times 10^8$ cfu/ml) and Listeria live cell suspensions in physiological saline (E1, $3.1 \times 10^4$ to $3.1 \times 10^9$ cfu/ml) were prepared. By using these live cell suspensions, Mycobacterium tuberculosis treated with isonicotinic acid hydrazide (INH, final concentration: 5 µg/ml) and rifampicin (REF, 150 µg/ml) for 3 months (D2), Mycobacterium tuberculosis treated with streptomycin (SM, 300 µg/ml) and kanamycin (KM, 300 µg/ml) for 3 months (D3), Mycobacterium tuberculosis treated with REF (150 µg/ml) and SM (300 µg/ml) for 3 months (D4), and Listeria monocytogenes treated with gentamycin (200 µg/ml) and ampicillin (500 µg/ml) for 3 weeks (E2) were prepared. D1 and E1 were immersed in boiling water for 12 minutes to prepare dead cells. The cells in all the samples mentioned above were classified into live cells, injured cells or dead cells by the ATP method and the esterase activity measurement method at the same bacterial densities, and it was examined that the various states of bacteria determined to be live cells, injured cells or dead cells by the method of the present invention in Example 6 belonged to which classification among those determined by the ATP method and the esterase method.

(2) Test Results and Discussion

Figure 18:
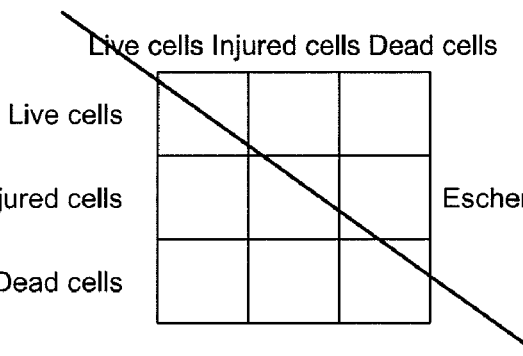
[FIG. 18] Graphs showing correspondence of classifications of live bacteria, injured bacteria and dead bacteria of *Escherichia coli, Staphylococcus epidermidis, Mycobacterium tuberculosis* and *Listeria* according to the esterase method, and distinction of the same according to the method of the present invention.

The results are shown in FIGS. 17 and 18. The results showed that, in comparison of the distinction abilities of the method of the present invention and the ATP method, the results of them completely coincided with each other as for Mycobacterium tuberculosis and Listeria, whereas as for Escherichia coli and Staphylococcus epidermidis, the cells determined by the ATP method to be in the state of dead cells were classified into injured cells and dead cells by the method of the present invention. Therefore, it is considered that delicate distinction of injured cells and dead cells can be performed by the method of the present invention with higher sensitivity.

Further, in the case of the esterase method, the esterase activity of Escherichia coli live cells was below the detection limit, and the esterase activity of Escherichia coli cells immersed in boiling water at 100° C. for 12 minutes and scientifically determined to be dead cells was higher than the detection limit. Therefore, it is considered that the measurement itself had a problem. In comparison of distinction abilities of the method of the present invention and the esterase method for the other bacteria, it was found that the results for Listeria mostly coincided with each other, whereas Staphylococcus epidermidis and Mycobacterium tuberculosis cells in a state determined to be dead cells by the esterase method were classified into two kinds of states, injured cells and dead cells, according to the method of the present invention. Therefore, it is considered that the method of the present invention is more suitable for delicate distinction of injured cells and dead cells.

Example 8

Detection of Live Cells in Clinical Samples (1) Preparation of Samples and Test Method Heparinized blood (type A) was collected from a healthy human subject, and a Listeria live cell suspension of $1.8 \times 10^8$ cfu/ml was diluted 10 times with the blood. The suspension was further serially diluted with the blood to prepare blood inoculated with $1.8 \times 10^3$ to $8 \times 10^7$ cfu/ml of Listeria monocytogenes (live cells).

Each of the blood not inoculated with Listeria (live cells) and blood inoculated with Listeria (live cells) was taken in a volume of 1 ml, 10 µl of a 1000 µg/ml EMA aqueous solution was added to each blood, and the mixture was maintained at 4° C. for 5 minutes under light shielding. Then, each sample was irradiated with visible light of 500 W for 5 minutes on ice. 750 µl of physiological saline, 200 µl of a 189 U/ml lipase solution and 10 µl of a 10000 U/ml deoxyribonuclease solution was added to each sample, and the sample was maintained at 30° C. for 30 minutes. Then, 40 µl of 1250 U/ml proteinase K was added to the sample, and the sample was maintained at 30° C. for 30 minutes. The total volume of the aforementioned EMA-treated blood was carefully overlaid on 2 ml of Ficoll Paque filled beforehand in a 15 ml volume polypropylene tube, and subjected to centrifugation at 100×g for 5 minutes. The supernatant was extracted in a volume of 1 ml and subjected to refrigerated centrifugation at 4° C. and 14000×g for 10 minutes, and the supernatant was removed. 200 µl of physiological saline and 0.6 µl of a nuclear stain agent (SYTO9/PI=1/1) was added to the residue, and the mixture was left at room temperature for 15 minutes under light shielding. Then, the mixture was subjected to refrigerated centrifugation at 4° C. and 14000×g for 10 minutes, the supernatant was removed, then 1 ml of physiological saline was added to the residue, the mixture was subjected to refrigerated centrifugation of the same condition, the supernatant was removed, and 200 µl of physiological saline was added to the residue to prepare a sample for FCM measurement.

The same procedure as that of the aforementioned method (referred to as the "EMA-LNP-FP method") was also performed in parallel except that the EMA treatment was not performed (referred to as the "LNP-FP method") to prepare a sample for FCM measurement.

(2) Test Results

Figure 19B:
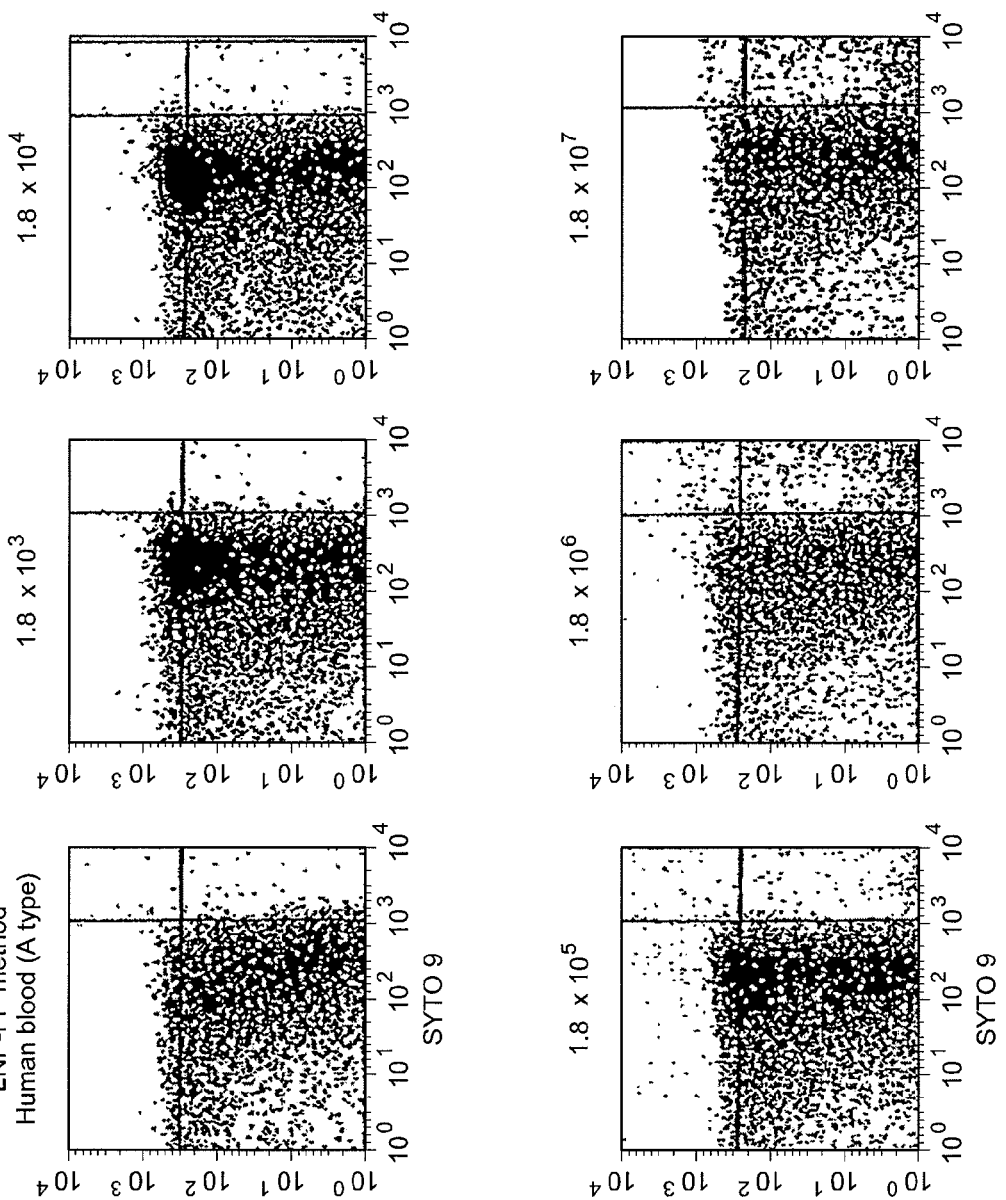
FIG. 19B shows EMA-LNP-FP method.

The results are shown in FIG. 19. In the EMA-LNP-FP method and the LNP-FP method, the number of plotted points corresponding to SYTO9(+) (intensity of $2 \times 10^3$ or higher) and PI(−) was proportional to the concentration of inoculated Listeria (live cells), and the detection limit of the Listeria monocytogenes (live cells) in blood was considered to be $1.8 \times 10^4$ cfu/ml. Further, since the plotted points of the contaminants corresponding to SYTO9(−) ·PI(−) were not shifted to the left direction by the EMA treatment, it was considered that they were not mononuclear cells such as monocytes and leucocytes, or lymphocytes called granulocytes. Since leucocytes do not have cell walls, but has only cell membranes, EMA penetrates into them even if the cells are not injured. Further, since the penetrated EMA inhibits re-ligation of chromosomal DNAs in leucocyte cells among cleavage and re-ligation of chromosomal DNAs by topoisomerase II, the chromosomal DNAs are cleaved everywhere, and that state is maintained. Therefore, the intercalation efficiency of SYTO9 into the chromosomal DNAs markedly decreases, and as a result, the plotted points are significantly shifted to the left direction. However, this phenomenon was not observed in this test.

Further, since erythrocytes not having chromosomal DNAs have the highest specific gravity among the blood cells, it cannot be considered that they contaminate into the supernatant even after the low speed centrifugation using Ficoll Paque, and in fact, they do not provide such plotted points of contaminants in the SYTO9/PI staining as those seen in this example. Furthermore, since the sample was treated with lipase, nuclease and proteinase K, lipids and complements remaining in blood in small amounts cannot be considered to constitute the contaminants, either.

From the above, the aforementioned contaminants are considered to be decomposition fragments of cell membranes generated by phagocytosis of a part of erythrocytes by *Listeria* or hemolysis of a part of erythrocytes. In this example, live cells can be detected to some extent, even if the EMA treatment was not performed. However, the size and the complexity of the internal structure of mononuclear cells such as monocytes and lymphocytes are close to those of bacteria, and they may show an SYTO9 and PI intensities similar to those of bacteria (live cells). Therefore, if they contaminate, they may be erroneously determined as live cells. Accordingly, it is more preferable to carry out the EMA treatment in view of accuracy. Further, since a lot of injured cells generated by antibiotics exist besides live cells in blood of sepsis patients with a hepatic function disorder, for example, the EMA treatment is required from the same aspect.

What is claimed is:

1. A kit for use in a method for preparing a measurement sample for detecting live cells, injured cells and dead cells of a microorganism in a test sample by flow cytometry, which comprises the following elements:
    an enzyme selected from lipolytic enzymes and proteases, which has an activity of decomposing cells other than those of the microorganism, colloidal particles of proteins or lipids existing in the test sample,
    a topoisomerase poison selected from the group consisting or amsacrine, camptothecin, doxorubicin, ellipticine, etoposide, mitoxantrone, saintopin, topotecan CP-115, 953 and ethidium monoazide and/or a DNA gyrase poison selected from the group consisting of ciprofloxacin, ofloxacin, enoxacin, pefloxacin, fleroxacin, norfloxacin, nalidixic acid, oxolinic acid and piromidic acid, and
    a first stain agent which stains live cells in different color from injured cells and dead cells, and a second stain agent which stains live cells and injured cells in different color from dead cells.

2. The kit according to claim 1, further comprising instructions for carrying out the method for preparing a measurement sample for detecting live cells, injured cells and dead cells of a microorganism in a test sample by flow cytometry, wherein the method comprises the following steps:
    a) treating the test sample with the enzyme selected from lipolytic enzymes and protesases,
    b) treating the test sample with the topoisomerase poison and/or the DNA gyrase poison,
    c) treating the test sample treated in steps a) and b) with the first stain agent and the second stain agent, and
    d) detecting the live cells, injured cells and dead cells of the microorganism in the test sample by flow cytometry.

3. The kit according to claim 1 or 2, wherein the first stain agent can penetrate cell walls of live cells, injured cells and dead cells, and the second stain agent more easily penetrates cell walls of dead cells than those of live cells and injured cells compared with the first stain agent.

4. The kit according to claim 1 or 2, wherein the the first stain agent is SYTO9 and the second stain agent is propidium iodide.

* * * * *

UNITED STATES PATENT AND TRADEMARK OFFICE
CERTIFICATE OF CORRECTION

| | | |
|---|---|---|
| PATENT NO. | : 8,241,866 B2 | Page 1 of 1 |
| APPLICATION NO. | : 12/832740 | |
| DATED | : August 14, 2012 | |
| INVENTOR(S) | : Yoshida et al. | |

It is certified that error appears in the above-identified patent and that said Letters Patent is hereby corrected as shown below:

ON THE TITLE PAGE:

(Item 57 Abstract) at line 10, Change "poison." to --poison,--.

IN THE SPECIFICATIONS:

In column 3 at line 28, Change "ethyophenanthradinium" to --ethylphenanthridinium--.

In column 5 at line 31, Change "poison." to --poison,--.

In column 7 at line 11, Change "(live bacteria injured bacteria)." to --(injured bacteria).--.

In column 14 at line 9 (approx.), Change "(1488 nm)" to --(λ488 nm)--.

In column 14 at line 10 (approx.), Change "is be" to --is--.

In column 18 at line 25, Change "SYTO9(+)'PI(-)" to --SYTO9(-)·PI(-)--.

In column 19 at line 41, Change "SYTO9(+)'PI(-)" to --SYTO9(-)·PI(-)--.

In column 35 at line 9, Change "SYTO9(-) ·PI(+)" to --SYTO9(-)·PI(+)--.

In column 36 at line 25, Change "$OD_{600\ nm}$," to --$OD_{600}$ nm,--.

In column 38 at line 11, Change "SYTO9(+)·PI(+)" to --SYTO9(±)·PI(±)--.

In column 38 at line 19, Change "(3-subunit" to --β-subunit--.

In column 38 at line 40-48, Delete "it is considered that,................Mycobacterium tuberculosis." And "DNAs are fragmented" as the continuation of the same paragraph.

In column 40 at line 46, Change "SYTO9(-) ·PI(-)" to --SYTO9(-)·PI(-)--.

In column 40 at line 53, Change "re-ligation" to --religation--.

In column 40 at line 54, Change "re-ligation" to --religation--.

IN THE CLAIMS:

In column 42 at line 15, In Claim 2, change "protesases," to --proteases,--.

In column 42 at line 27, In Claim 4, after "wherein" delete "the".

Signed and Sealed this
Nineteenth Day of March, 2013

Teresa Stanek Rea
*Acting Director of the United States Patent and Trademark Office*